(12) United States Patent
Tanaka et al.

(10) Patent No.: US 7,569,012 B2
(45) Date of Patent: Aug. 4, 2009

(54) ULTRASONIC ENDOSCOPE

(75) Inventors: Toshizumi Tanaka, Saitama (JP); Hiromu Itoi, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 743 days.

(21) Appl. No.: 11/172,849

(22) Filed: Jul. 5, 2005

(65) Prior Publication Data
US 2006/0009681 A1 Jan. 12, 2006

(30) Foreign Application Priority Data

| Jul. 6, 2004 | (JP) | 2004-199344 |
| Aug. 26, 2004 | (JP) | 2004-246274 |
| Nov. 5, 2004 | (JP) | 2004-321587 |

(51) Int. Cl.
*A61B 1/06* (2006.01)
*A61B 1/04* (2006.01)

(52) U.S. Cl. .............. 600/129; 600/160; 600/130; 600/437

(58) Field of Classification Search .......... 600/104, 600/109, 113, 121, 122, 129, 130, 139, 153, 600/160, 407, 437, 443, 447, 459, 462, 472
See application file for complete search history.

(56) References Cited

U.S. PATENT DOCUMENTS

| 4,763,662 | A | * | 8/1988 | Yokoi ............... 600/461 |
| 4,936,307 | A | * | 6/1990 | Saito et al. ........... 600/463 |
| 5,020,539 | A | * | 6/1991 | Yokoi et al. .......... 600/116 |
| 5,499,630 | A | * | 3/1996 | Hiki et al. ............ 600/461 |
| 5,505,205 | A | * | 4/1996 | Solomon et al. ....... 600/459 |
| 5,938,614 | A | | 8/1999 | Sakamoto |
| 6,149,598 | A | * | 11/2000 | Tanaka ............... 600/462 |
| 6,461,304 | B1 | * | 10/2002 | Tanaka et al. ......... 600/462 |
| 6,511,431 | B2 | * | 1/2003 | Ohara et al. .......... 600/453 |
| 2001/0041841 | A1 | | 11/2001 | Ohara et al. |
| 2002/0062083 | A1 | | 5/2002 | Ohara et al. |

FOREIGN PATENT DOCUMENTS

| JP | 2001-314403 | 11/2001 |
| WO | WO 03/011139 A1 | 2/2003 |

OTHER PUBLICATIONS

U.S. Appl. No. 11/172,849, filed Jul. 5, 2005, Tanaka et al.
U.S. Appl. No. 11/190,971, filed Jul. 28, 2005, Tanaka et al.

* cited by examiner

*Primary Examiner*—John P Leubecker
*Assistant Examiner*—Samuel Candler
(74) *Attorney, Agent, or Firm*—Oblon, Spivak, McClelland, Maier & Neustadt, P.C.

(57) ABSTRACT

An ultrasonic endoscope comprises an insertion portion comprising a distal hard portion which has: an endoscopic observation unit; and an ultrasonic observation unit having ultrasonic transducers arranged circumferentially on an outer circumferential section of the distal hard portion, wherein the ultrasonic observation unit comprises an ultrasonic-wave transmission/reception unit having an tunnel-shaped path which has an inner circumferential surface formed as a backing layer; a distal block is arranged on a distal side in an axial direction of the distal hard portion with respect to a location where the ultrasonic-wave transmission/reception unit is arranged, and distal ends of respective members constituting the endoscopic observation unit are fixed to the distal block; and part of the members which constitute the endoscopic observation unit are fitted so as to be partially protruded from an inside diameter of the tunnel-shaped path toward an outer circumferential side thereof.

9 Claims, 13 Drawing Sheets

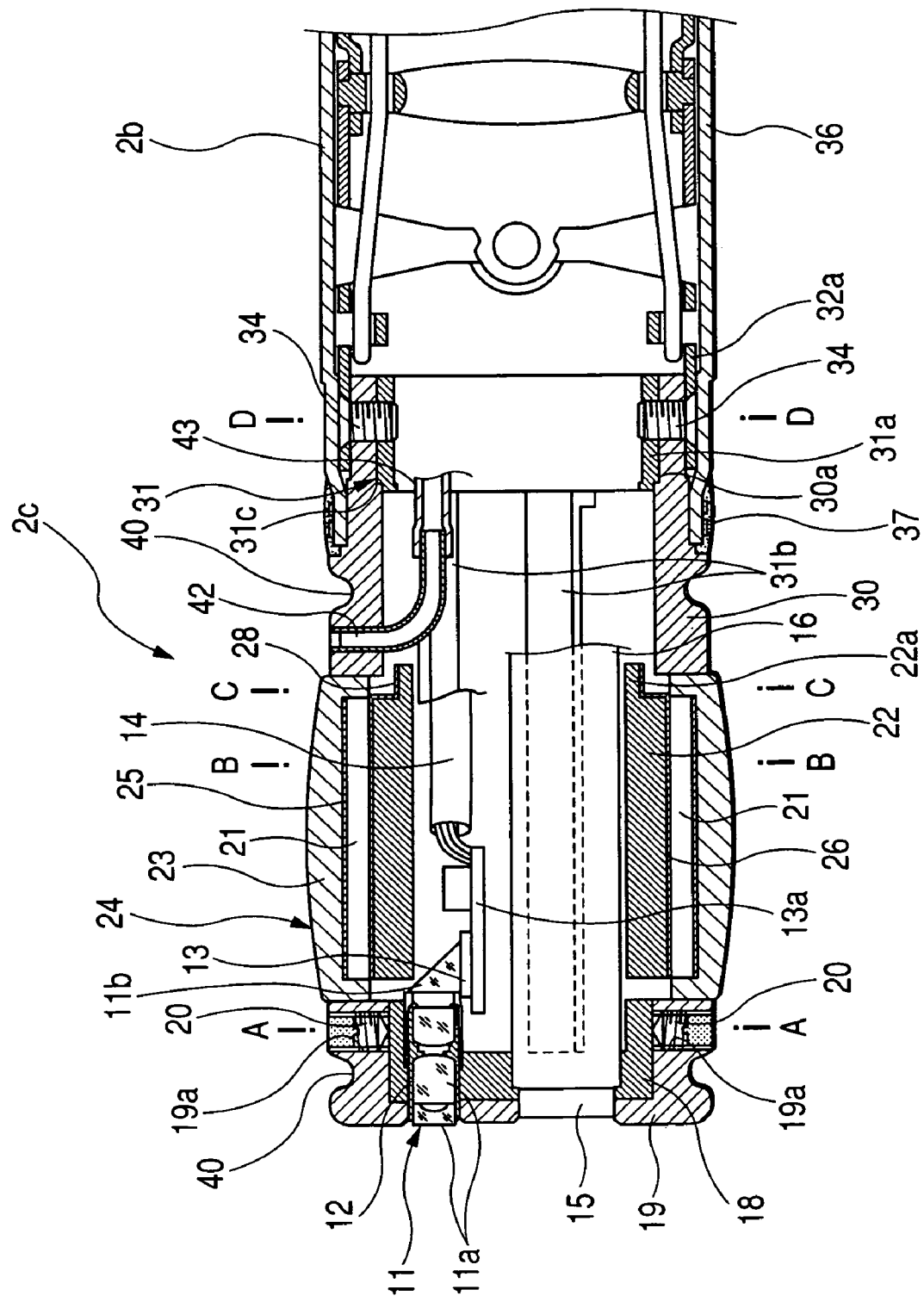

ULTRASONIC ENDOSCOPE

BACKGROUND OF THE INVENTION

1. Field of the Invention

The present invention relates to an ultrasonic endoscope whose insertion portion includes a distal hard portion which has an endoscopic observation unit having an observation field of view forwardly of the endoscopic observation unit, and an electronic scanning type of an ultrasonic observation unit having a circular or arcuate ultrasonic scanning plane perpendicular to the axis of the distal hard portion.

2. Description of the Related Art

A so-called electronic scanning type of ultrasonic endoscope has heretofore been widely used in which endoscopic observation means for observing a body cavity, an endoscopic mechanism including other means such as a treatment equipment insertion path through which to insert forceps or other treatment equipments, and ultrasonic observation means are fitted in a distal hard portion of an insertion portion and the ultrasonic observation means performs scanning by sequentially driving a multiplicity of ultrasonic transducers arranged in a predetermined direction in the ultrasonic observation means. For example, JP-A-2001-314403 describes a direct-view endoscope which has a field of view forwardly of a distal hard portion of its insertion portion as an observation field of view in the endoscopic observation means and in which the ultrasonic observation means has an ultrasonic scanning plane in its radial direction, i.e., a circular ultrasonic scanning plane or an ultrasonic scanning plane which is arcuate in a predetermined angular range.

The ultrasonic endoscope described in JP-A-2001-314403 is inserted into a body cavity tube, for example, an upper gastrointestinal tract such as the esophagus or the small intestine, or a lower gastrointestinal tract such as the large intestine, and an area which appears forward in the insertion direction is observed by the endoscopic observation means. If an area of interest such as an lesion is detected, the ultrasonic observation means is positioned to face the area of interest so that information about body tissues in the area can be acquired.

In the ultrasonic endoscope having the construction described in JP-A-2001-314403, members constituting the endoscopic observation means, at least an illumination section and an observation section, a treatment equipment insertion channel through which treatment equipments such as forceps are to be inserted, and other members such as an air/water supply tube for cleaning the observation section are arranged so as to face the distal end surface of the distal hard portion. Since the ultrasonic observation means performs radial ultrasonic scanning, the ultrasonic observation means has an approximately cylindrical shape and a tunnel-shaped path is formed in the inside of a section in which the ultrasonic observation means is fitted, and the members constituting the endoscopic observation means are arranged in the inside of the tunnel-shaped path.

The ultrasonic observation means which performs radial ultrasonic electronic canning has a multiplicity of ultrasonic transducers arranged in a cylindrical or arcuate form, and at least an acoustic lens, more strictly, an acoustic matching layer and an acoustic lens are provided on a transmission/reception surface side, i.e., an outer circumferential side, of the ultrasonic transducers. Backing materials are arranged on a surface opposite to the transmission/reception surface of the ultrasonic transducers. Accordingly, the inner circumferential surface of the backing material forms the inside diameter of the tunnel-shaped path. All the members constituting the endoscopic observation means must be arranged in a predetermined arrangement relationship so that all the members are housed in the tunnel-shaped path.

The thickness dimension of each of the ultrasonic transducers constituting the endoscopic observation means, and the thickness dimension of the acoustic lens as well as the thickness dimension of the backing material are respectively set in functional terms. The size of each of the members constituting the endoscopic observation means, for example, the sizes of an illumination lens and a light guide which constitute an illumination section, the size of an objective lens constituting the observation section, the size of a lens barrel for the objective lens, the size of a solid-state image pickup device, the size of a circuit board for the solid-state image pickup device, and the cross-sectional size of the treatment equipment insertion channel must be those necessary to realize their functions. Accordingly, if the sizes of the respective members constituting the ultrasonic observation means and the endoscopic observation means are made equivalent to dimensions necessary for their respective functions, the outside diameter of the distal hard portion increases and the operationality with which the distal hard portion is to be inserted into a body cavity is not only degraded, but also a large burden is imposed on a subject. On the other hand, if the outside diameter of the distal hard portion is to be reduced, any one or a plurality of members constituting the ultrasonic observation means or the endoscopic observation means must be reduced in size, so that functional restrictions arise.

The invention has been made in view of the above-mentioned problems, and an object of the invention is to make it possible to minimize the outside diameter of the distal hard portion in the insertion portion without reducing to an unnecessary extent the size of each of members constituting the ultrasonic observation means and the endoscopic observation means.

An ultrasonic transducer array is generally made of an approximately cylindrical unit, and a backing layer is arranged in the inside of ultrasonic transducers, while an acoustic lens is fitted on the outside of the ultrasonic transducers. The acoustic lens serves to focus ultrasonic beams transmitted from the ultrasonic transducers, and beams in directions perpendicular to an ultrasonic-wave transmission plane are improved by the acoustic lens. The ultrasonic transducer array is integrated with the above-mentioned members and the like and is incorporated in the distal hard portion of the insertion portion, and each member constituting the endoscopic observation means and the like is inserted through the inside of the ultrasonic transducer array formed in a cylindrical shape in this manner, specifically, a tunnel-shaped path formed in the inside of the backing layer.

According to the above-mentioned related art, a tubular support member is provided in the inside of the distal hard portion of the insertion portion and a tubular support member is provided in the inside of the distal hard portion. The ultrasonic transducer array is secured in such a manner that the ultrasonic transducer array is fitted on the support member and the ultrasonic transducer array are clamped on the distal and proximal opposite ends thereof. Stopper means for the ultrasonic transducer array is provided on one of distal and proximal clamping members. The ultrasonic transducer array is fixed to the inside support section and to the distal and proximal clamping members by an adhesive so that the air-tightness of joining sections can be ensured. Accordingly adhesion sections on the opposite ends of the ultrasonic transducer array are exposed to the outside, and the adhesive in this exposed section is degraded by heat treatment during sterilization of the insertion portion or by immersion of the insertion portion into an antiseptic solution. This degradation causes problems such as lowering of seal functions of the adhesion sections.

In this construction, the acoustic lens is a member which constitutes the external circumferential section of the ultrasonic transducer array, and if a material which is higher in sonic speed than living bodies is used as the material of the acoustic lens, the acoustic lens is constructed as a concave lens, while if a material which is lower in sonic speed than living bodies is used as the material of the acoustic lens, the acoustic lens is constructed as a convex lens. The acoustic lens is desirably constructed from a convex lens in terms of adhesiveness to the internal walls of body cavities. The sonic speed of silicone rubber is about 1000 m/sec, and the sonic speed of living bodies is 1530 m/sec. Accordingly, silicone rubber can be used as the material of the acoustic lens.

The invention has been made in view of the above-mentioned problems, and an object of the invention is to reduce the number of joining sections to be exposed from the outside surface of a section in which an ultrasonic transducer array is fitted.

The insertion portion of the ultrasonic endoscope is inserted into the body of a subject for the purposes of various examinations and treatments, so that the diameter of the insertion portion need be made as thin as possible. If the accuracy of examination by the ultrasonic observation means is to be increased, it is necessary to increase the size of each of the ultrasonic transducers so as to increase the output power thereof. Accordingly, not only the thickness of each of the ultrasonic transducers increases, but also the thickness of the backing layer must be increased. The endoscopic mechanism is inserted in the tunnel-shaped path formed in the inside of the backing layer.

The endoscopic mechanism needs at least an illumination section and an observation section because the endoscopic mechanism is used to optically observe body cavities. There is also a case where other members such as a treatment equipment insertion channel and a cleaning-fluid supply tube for an observation window are provided in the endoscopic mechanism. In the observation section in particular, there is a case where an objective lens and a solid-state image pickup device as well as, if necessary, various filters and a prism for bending an optical path are provided. The treatment equipment insertion channel is constructed to allow forceps and other treatment equipments to be inserted through, and is desirably made of a thick tube in order to allow insertion of large-sized treatment equipments.

As described above, the ultrasonic endoscope has the problem that if any of the functions of the ultrasonic observation means or the endoscopic mechanism is to be improved, the insertion portion must be made thick as needed. The inside diameter of the backing layer in particular has an extremely large influence on the fitting of the endoscopic mechanism. An object of the invention is to make it possible to ensure a wide fitting space for the endoscopic mechanism by making as wide as possible the cross section of the tunnel-shaped path formed by the backing layer.

SUMMARY OF THE INVENTION

To achieve the above object, the invention provides an ultrasonic endoscope which comprises an insertion portion comprising a distal hard portion which has: an endoscopic observation unit having an observation field of view forwardly of the endoscopic observation unit; and an ultrasonic observation unit having a predetermined number of ultrasonic transducers arranged circumferentially on an outer circumferential section of the distal hard portion and having a circular or arcuate scanning range, wherein the ultrasonic observation unit comprises an ultrasonic-wave transmission/reception unit having an approximately cylindrical tunnel-shaped path which has an inner circumferential surface formed as a backing layer; a distal block is arranged on a distal side in an axial direction of the distal hard portion with respect to a location where the ultrasonic-wave transmission/reception unit is arranged, and distal ends of respective members constituting the endoscopic observation unit are fixed to the distal block; and part of the members which constitute the endoscopic observation unit are fitted so as to be partially protruded from an inside diameter of the tunnel-shaped path toward an outer circumferential side of the tunnel-shaped path in the distal block.

Part of the members constituting the endoscopic observation means are changed in cross-sectional shape in the axial direction in a portion located in the distal hard portion. For example, an illumination lens constituting an illumination section is larger in diameter than a light guide constituting the same. In an observation section, an objective lens, because it is made of a plurality of lenses, is fitted in a lens barrel, and the cross-sectional shape of the lens barrel is circular, but a solid-state image pickup device arranged at an image-forming position of the objective lens is planar and is mounted on a circuit board. In addition, signal cables are led from the circuit board. Therefore, the lens barrel differs in shape and dimension from members arranged on a proximal side from the lens barrel. For this reason, the distal block is extended forwardly from an area in which the tunnel-shaped path is formed in the ultrasonic observation means. Accordingly, the outside diameter of the distal block can be made approximately the same as the outside diameter of the ultrasonic observation means. In addition, as mentioned above, a section whose distal end is protruded toward the outer circumferential side from a section located in the inside of the tunnel-shaped path is provided in the distal block enlarged in diameter in the above-mentioned manner. Accordingly, the dependency of the endoscopic observation means on the tunnel-shaped path can be solved, and even if each of the members is given a size which allows them to effectively perform their functions, the distal hard portion does not become thick in diameter. In addition, the distal block can be constructed of an endoscope fitting member formed of a metallic material in terms of strength and workability, and a distal cap made of an insulative member fitted so as to prevent the endoscope fitting member from being exposed to the outside, so that the members constituting the endoscopic observation means can be fixed to the distal block. At at least a position where the distal cap is fitted, the illumination section or the observation section is increased in diameter so as to be partially protruded from the inside diameter of the tunnel-shaped path. In the illumination section in particular, a section inserted in the tunnel-shaped path can be arbitrarily deformed in cross section, so that the section inserted can be, for example, bypassed so as not to interfere with other members.

Preferably, the part of the members fitted so as to be partially protruded from the inside diameter of the tunnel-shaped path is at least one of an illumination section and an observation section.

Preferably, the illumination section comprises an illumination lens and a light guide, the illumination lens having an outside diameter partially protruded from the tunnel-shaped path, the light guide being inserted through the tunnel-shaped path while being deformed into a flattened shape.

Preferably, the distal block comprises: an endoscope fitting member comprising a metallic material; and a distal cap fitted so as to prevent the endoscope fitting member from being exposed to the outside, so that the members constituting the endoscopic observation unit are fixed to the distal block, and at a position where the distal cap is fitted, at least one of the illumination section and the observation section is increased in diameter so as to be partially protruded from the inside diameter of the tunnel-shaped path.

By adopting the above-mentioned construction, it is possible to arrange any of the members constituting the endoscopic observation means on the outer circumferential side from the tunnel-shaped path without allowing any of the members to interfere with the ultrasonic observation means, whereby it is possible to provide the advantage of thinning the diameter of the distal hard portion of the insertion portion.

There may be provided an ultrasonic endoscope, wherein the insertion portion further comprises an angle portion connected to the distal hard portion, an acoustic lens fitted to surround a ultrasonic transducer array in which the ultrasonic transducers are arranged and a sheath layer of the angle portion are fitted on the insertion portion as an integrated external sleeve.

The acoustic lens may be a concave lens, but can also be constructed as a convex lens in terms of adhesiveness to the inner walls of body cavities. A material which propagates ultrasonic waves at lower speed than the body does is, for example, silicone rubber. On the other hand, the sheath layer of the angle portion needs to have stretchability and must be superior in weather resistance, chemical resistance and the like. A preferred example of such material is silicone rubber. Accordingly, for example, silicone rubber can be used as the external sleeve which is fitted on the outermost circumference so as to extend from the angle portion of the insertion portion to the distal hard portion. The external surface of a section in which the ultrasonic transducer array is fitted is be swollen into a convex shape so that the external sleeve can function as the acoustic lens.

When the angle portion is operated to bend, the sheath layer of the angle portion is stretched. On the other hand, a section which serves as the acoustic lens needs to be held so that its external surface shape does not vary. In the distal hard portion, if a variation occurs in the external surface shape of the section in which the ultrasonic transducer array in particular is fitted, a variation occurs in the characteristics and function of the acoustic lens. For this reason, it is desirable that a tension transmission/reception section comprising, for example, a bobbin and adhesive coating be provided at the boundary between the sheath layer and the acoustic lens which constitute the external sleeve. The external sleeve is a member having electrical insulation characteristics. The endoscopic observation unit comprises members comprising at least an illumination section and an observation section, the endoscopic observation unit being disposed to a distal end surface of the distal hard portion. Each of members that constitutes the endoscopic observation means is fitted in an endoscope fitting section made of a metallic material provided at the distal end of the distal hard portion, and a distal cover section which covers the endoscope fitting section can also be formed integrally with the distal end of the acoustic lens of the external sleeve.

According to the above-described construction, since a joining section between distal and proximal members is not exposed to the outside in any area from the angle portion constituting the insertion portion to the distal hard portion, it is possible to achieve the advantage of increasing the airtightness of the inside of the ultrasonic endoscope.

There may be provided an ultrasonic endoscope, wherein the endoscopic observation unit comprises at least an illumination section and an observation section, the endoscopic observation unit being disposed to a distal end surface of the distal hard portion; an endoscopic mechanism, which comprises: the endoscopic observation unit; and other sections including a treatment equipment insertion channel, is inserted in an inside of the tunnel-shaped path; and a filler which is the same as or close to the backing layer in acoustic impedance is charged in a spatial area which is produced in a section where the endoscopic mechanism is arranged in the inside of the backing layer.

Preferably, the filler comprises the same material as the backing layer and a solid-state image pickup device is provided in the observation section, at least part of the solid-state image pickup device being embedded in an inside of the filler.

Accordingly, since the filler can serve a function similar to the backing layer, it is possible to reduce the thickness of the backing layer which constitutes the ultrasonic observation means, and it is possible to achieve advantages such as widening the fitting space for the endoscopic mechanism by the corresponding amount.

BRIEF DESCRIPTION OF THE DRAWINGS

FIG. 4A is a vertical cross-sectional view of the distal hard portion (first embodiment);

DETAILED DESCRIPTION OF THE INVENTION

Figure 1:
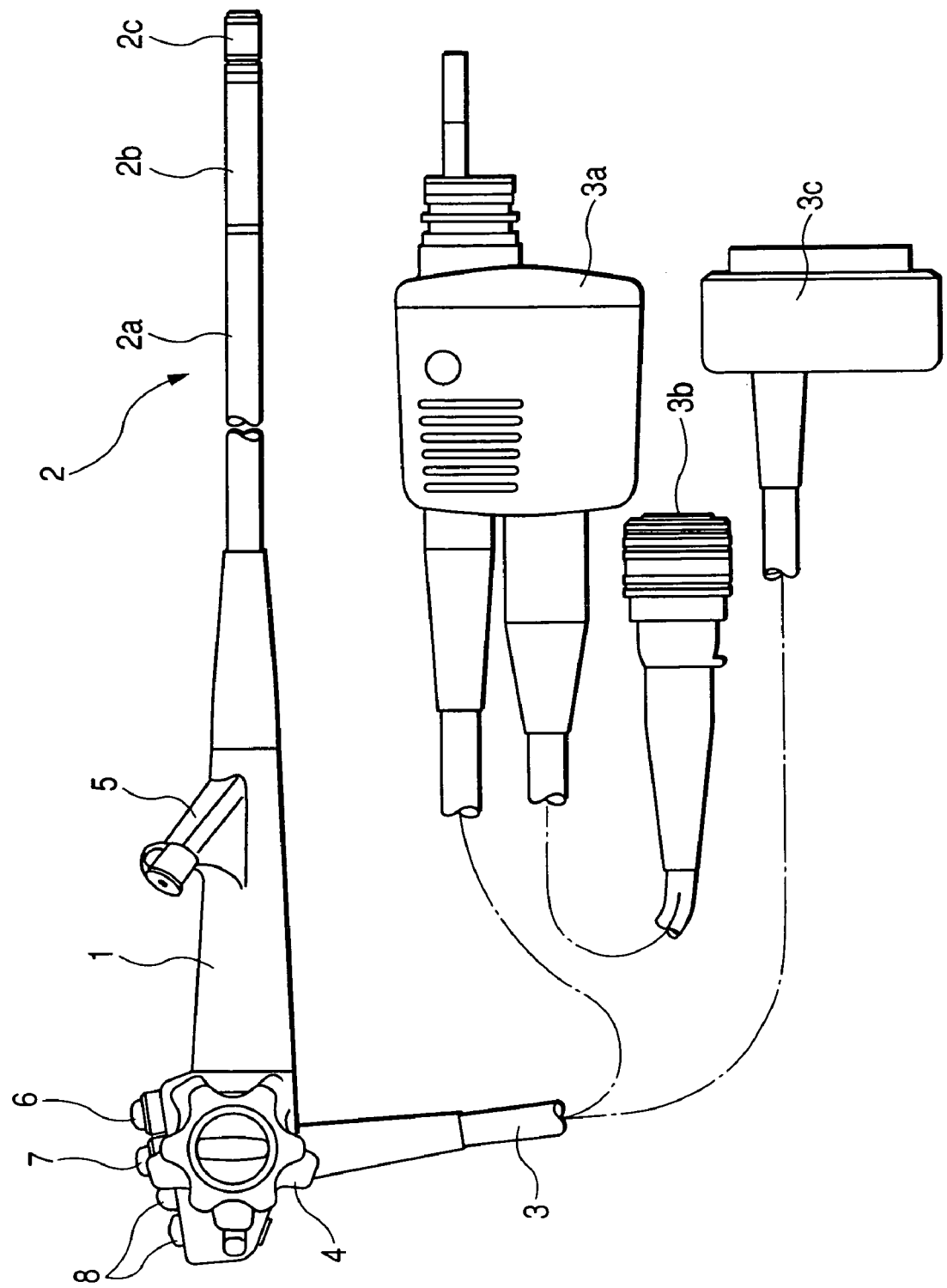
FIG. 1 is a general construction diagram showing an ultrasonic endoscope according to one preferred embodiment of the invention.

A preferred embodiment of the invention will be described below in detail with reference to the accompanying drawings. As shown in FIG. 1, an ultrasonic endoscope is generally made of a main control portion 1, an insertion portion 2, and a universal cord 3. A light source device, a video signal processing device and an ultrasonic observation device are connected to the ultrasonic endoscope so as to constitute the entire system. The universal cord 3 is extended from the main control portion 1 and is divided at a halfway position into branches which are respectively equipped with a connector 3a removably connected to the light source device, a connector 3b removably connected to the video signal processing device, and a connector 3c removably connected to the ultrasonic observation device.

The main control portion 1 can be grasped in one hand by an operator or the like, and is provided with an angle operation section 4 and a treatment equipment guiding portion 5 and is also equipped with an air/water feed button 6, an suction button 7 and other switches 8.

The insertion portion 2 is a cord-like member joined to the main control portion 1 and having a predetermined length, and is inserted into the body of a subject and the like. In this insertion portion 2, nearly all length extending from a position where the insertion portion 2 is joined to the main control portion 1 is formed as a flexible portion 2a having a structure arbitrarily bendable along an insertion path in a body cavity and the like. An angle portion 2b is joined to the distal end of the flexible portion 2a, and a distal hard portion 2c is joined to the angle portion 2b. The angle portion 2b can be bent upwardly, downwardly, leftwardly and rightwardly by remote operation in order to direct, the distal hard portion 2c in a desired direction. Accordingly, the main control portion 1 is provided with the angle operation section 4 so that the angle portion 2b can be bent by the operation of the operator so as to direct the distal hard portion 2c in a desired direction.

Figure 2A:
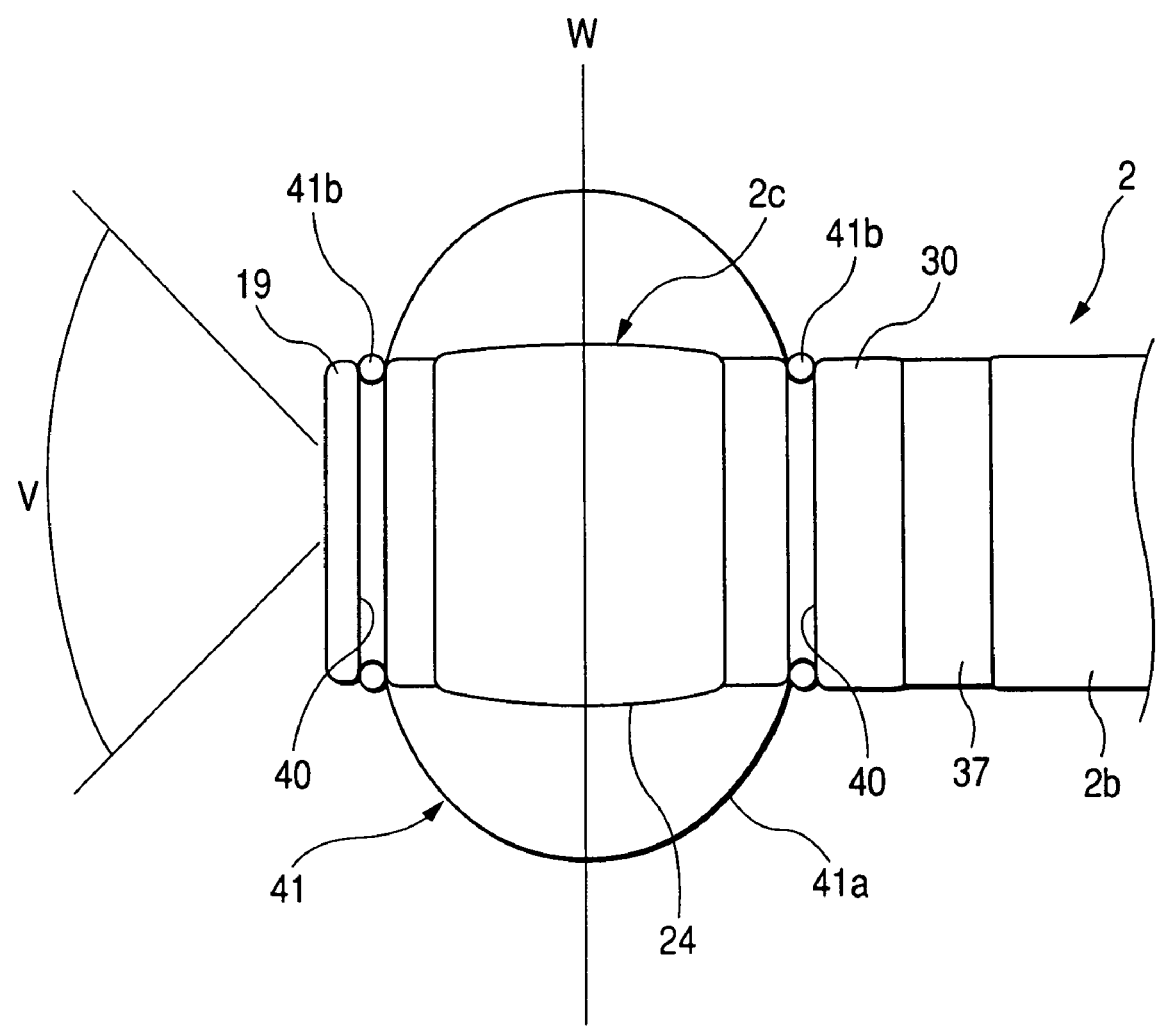
FIG. 2A is a schematic view of an external appearance of a distal end of an insertion portion of the ultrasonic endoscope according to the preferred embodiment of the invention.
Figure 2B:
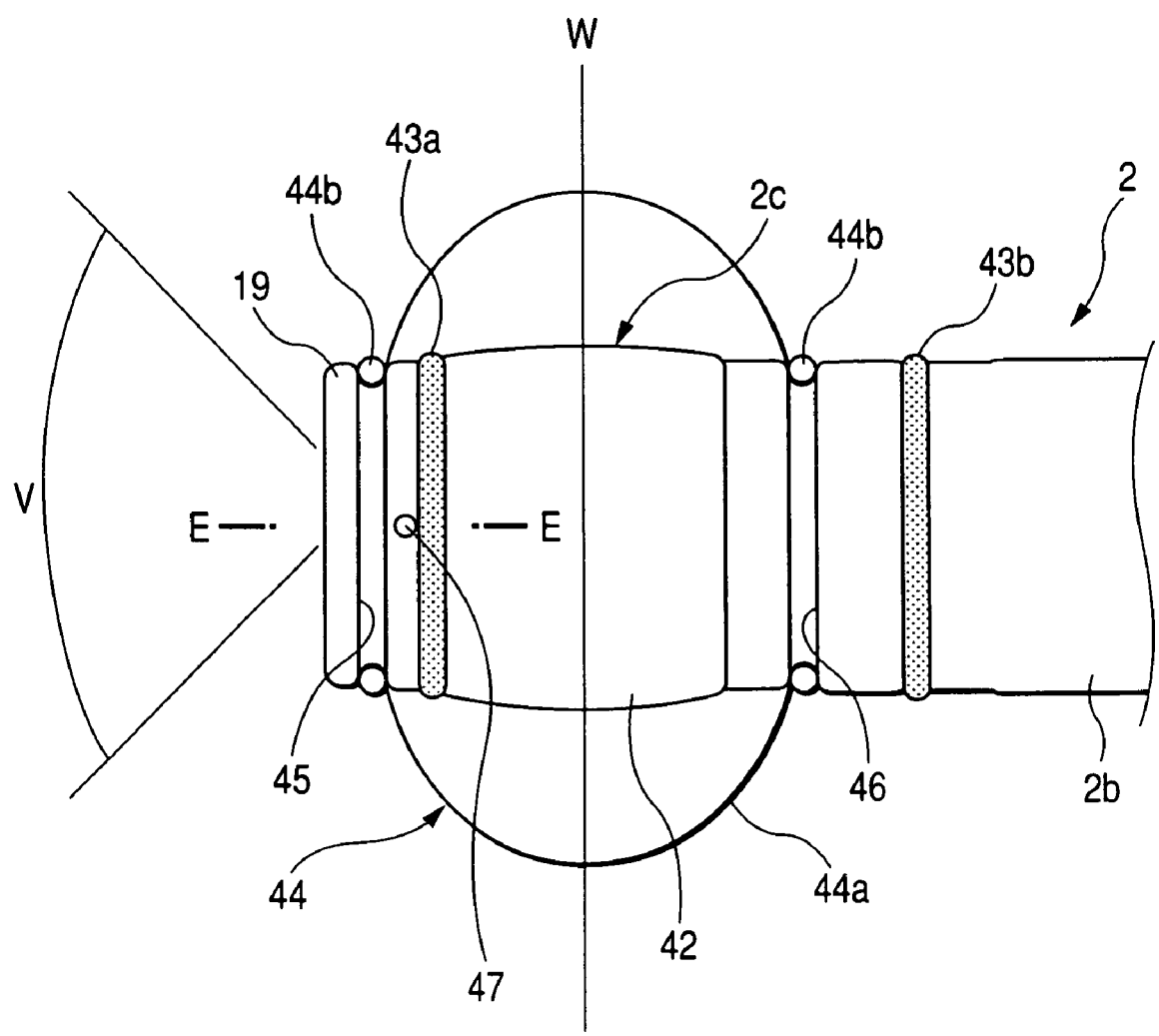
FIG. 2B is a schematic view of an external appearance of a distal end of an insertion portion of the ultrasonic endoscope according to the preferred embodiment of the invention.
Figure 3:
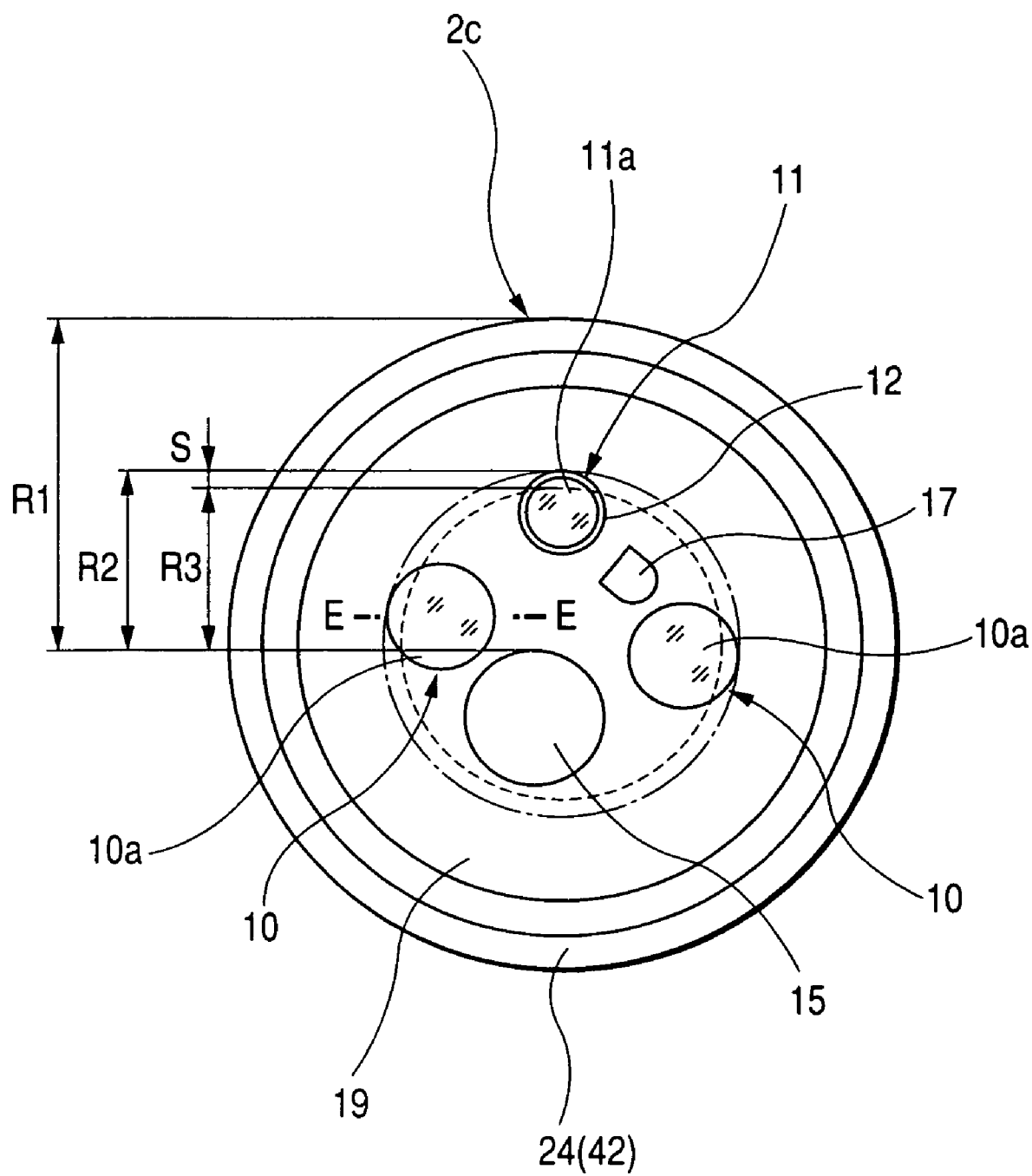
FIG. 3 is a schematic view showing a distal end surface of a distal hard portion of the ultrasonic endoscope according to the preferred embodiment of the invention.

FIGS. 2A and 2B show different embodiments of a distal end of the insertion portion 2, and FIG. 3 shows the construction of a distal end surface of the distal hard portion 2c. As is apparent from FIGS. 2 and 3, the distal hard portion 2c is provided with an endoscopic observation unit which has a field of view with a predetermined viewing angle V in the extension direction of the axis of the distal hard portion 2c, i.e., forwardly of the distal hard portion 2c, and an electronic radial scan type of ultrasonic observation unit having a circular or arcuate ultrasonic scanning plane W at a position displaced toward a proximal side from the field of view of the endoscopic observation unit.

Figure 4B:
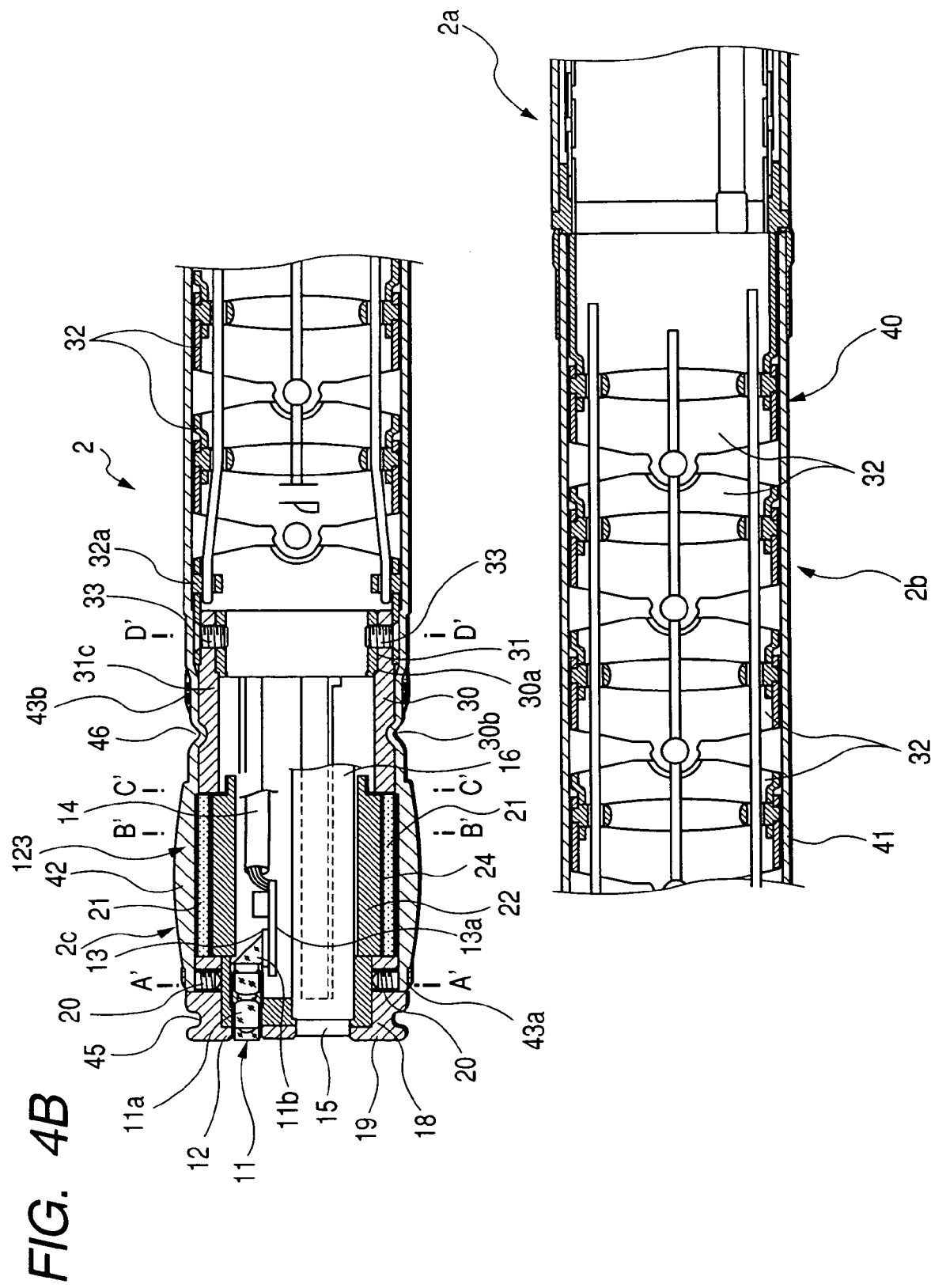
FIG. 4B is a vertical cross-sectional view of an angle portion of the insertion portion and a distal end extending from the angle portion (second embodiment)
Figure 5A:
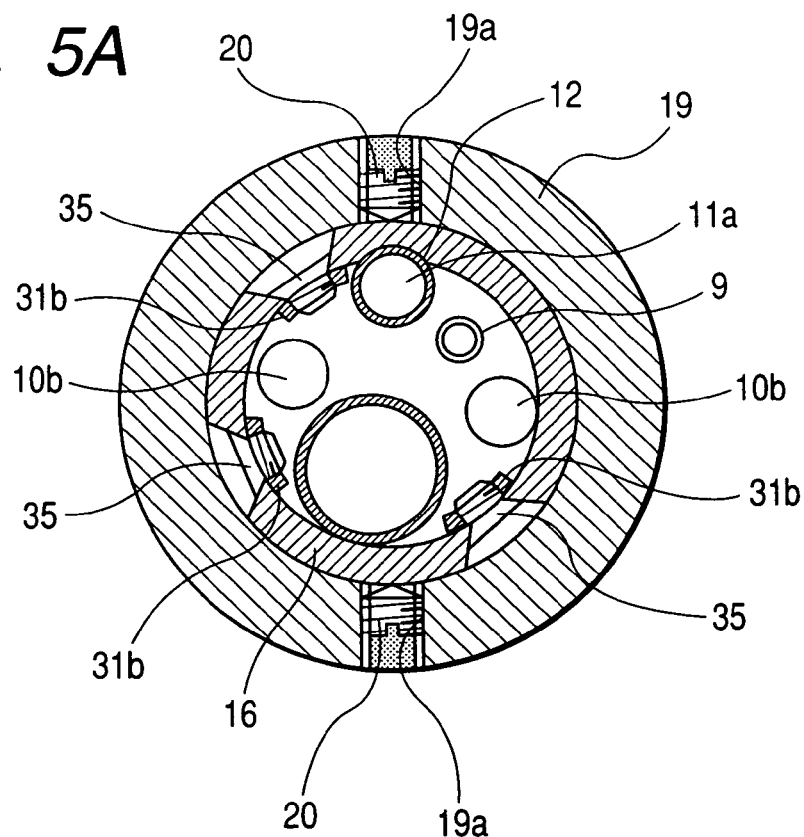
FIG. 5A is a cross-sectional view taken along line A-A of FIG. 4A.
Figure 5B:
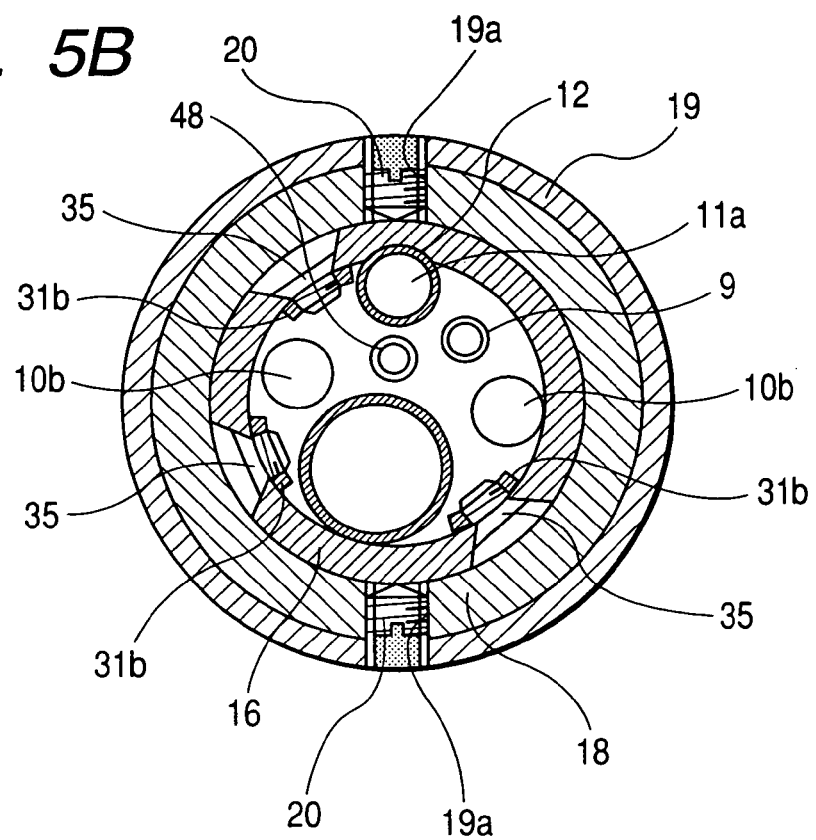
FIG. 5B is a cross-sectional view taken along line A'-A' of FIG. 4B.
Figure 6A:
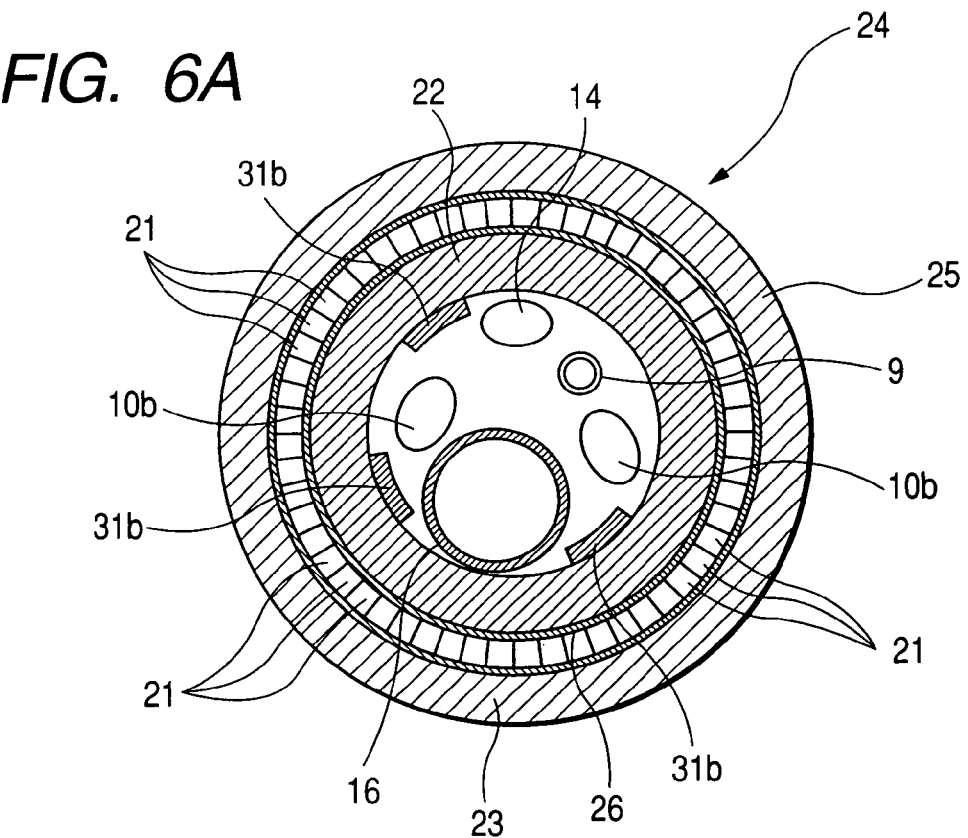
FIG. 6A is a cross-sectional view taken along line B-B of FIG. 4A.
Figure 6B:
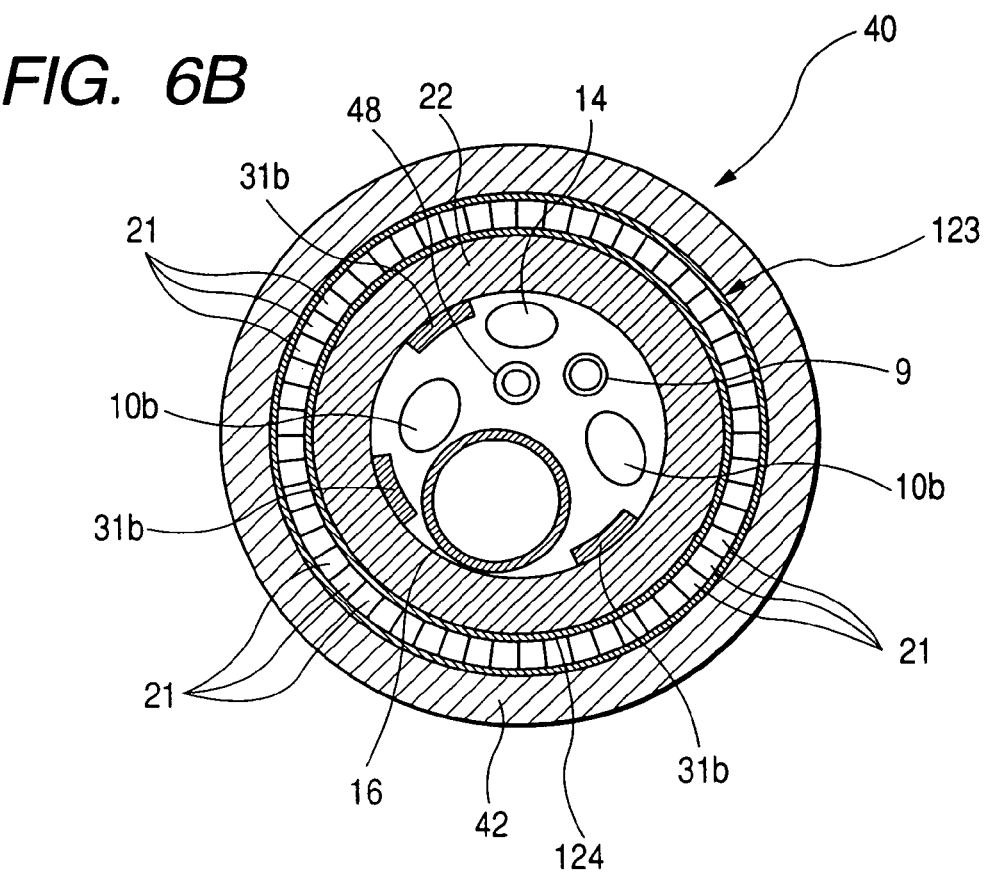
FIG. 6B is a cross-sectional view taken along line B'-B' of FIG. 4B.

FIG. 4A shows a cross section of the first embodiment of the distal end of the insertion portion 2. FIG. 4B shows a cross section of the second embodiment of the distal end of the insertion portion 2. As is apparent from FIGS. 3 and 4, the endoscopic observation unit is made of illumination sections 10 and an observation section 11, and the respective illumination sections 10 are arranged at opposite positions between which the observation section 11 is positioned. Each of the illumination sections 10 is made of an illumination lens 10a and a light guide 10b (refer to FIGS. 5A to 8B) which face the distal end surface of the distal hard portion 2c. The light guide 10b is made of an optical fiber bundle, and is extended from the connector 3a of the universal cord 3 to the distal hard portion 2c of the insertion portion 2 so that its illumination light emission end faces a position which opposes the illumination lens 10a. On the other hand, the observation section 11 is made of an objective lens 11a and a prism 11b which bends an optical path entering from the objective lens 11a at 90°, and the objective lens 11a is provided in a lens barrel 12 and the prism 11b is provided in the state of being fixed to the lens barrel 12. A solid-state image pickup device 13 is joined to the prism 11b, and a predetermined number of signal lines are connected to a circuit board 13a of the solid-state image pickup device 13. These signal lines are bundled and extended to the connector 3b of the universal cord 3.

The distal end surface of the distal hard portion 2c of the insertion portion 2 is provided with a treatment equipment lead-out opening 15 through which to pass forceps and other treatment equipments, and the treatment equipment lead-out opening 15 is fitted with a connection pipe 16 to which a treatment equipment insertion tube extending from a treatment equipment guiding portion 5 provided in the main control portion 1 is connected. The treatment equipment insertion tube is constructed to meet a suction path in the inside of the main control portion 1. Furthermore, the distal hard portion 2c is fitted with a nozzle 17 for cleaning the distal end surface of the objective lens 11a in the observation section 11 when it is contaminated by a body fluid. A cleaning-fluid supply tube 9 to be operated through the air/water feed button 6 is connected to the nozzle 17. Accordingly, these members also function as an endoscopic mechanism constituting an endoscope together with the endoscopic observation unit.

The endoscopic observation unit is constructed in the above-described manner, and the distal ends of the respective members constituting the endoscopic observation unit are fixedly held by an endoscope fitting member 18. The endoscope fitting member 18 is made of a metallic material, such as stainless steel, in which are formed a plurality of through-holes through which to insert the respective members constituting the above-mentioned endoscopic observation unit. A distal cap 19 is fitted on the endoscope fitting member 18 so as to prevent the endoscope fitting member 18 made of the metallic material from being exposed to the outside. The endoscope fitting member 18 and the distal cap 19 constitute a distal end block. As shown in FIG. 5, two screw holes 19a are formed to extend through the distal cap 19 in the thickness direction thereof, and set screws 20 are respectively screwed into the screw holes 19a so that the distal ends of the set screws 20 are pressed against the endoscope fitting member 18 and the abutment surfaces between the endoscope fitting member 18 and the distal cap 19 are joined together. In this manner, the distal end block made of the endoscope fitting member 18 and the 19 is integrated.

The ultrasonic observation unit having a radial scanning plane is provided in the distal hard portion 2c at a proximal position of the distal cap 19. As is apparent from FIGS. 6A and 6B, the ultrasonic observation unit includes a multiplicity of ultrasonic transducers 21 which are arranged in the circumferential direction so that their transmission/reception surfaces are directed in the axial direction of the distal hard portion 2c, and the ultrasonic transducers 21 are arranged in a circumferential or arcuate form (for example, approximately 270°) so as to perform electronic scanning. A backing material (backing layer) 22 is fitted on the inner circumferential side of the ultrasonic transducers 21 arranged in this manner, while an acoustic lens 23 is fitted on the outer circumferential side of the ultrasonic transducers 21. As shown in FIG. 4A, the multiplicity of ultrasonic transducers 21, the backing material 22 and the acoustic lens 23 constitute an ultrasonic wave transmission/reception unit 24. In addition, a backing layer 22 is fitted on the inner circumferential side of the ultrasonic transducers 21 arranged in this manner. The multiplicity of ultrasonic transducers 21 are fixed to the backing layer 22 by means of adhesion or the like, thereby constituting an ultrasonic transducer array 123 having a generally cylindrical shape (See FIG. 4B).

Figure 7A:
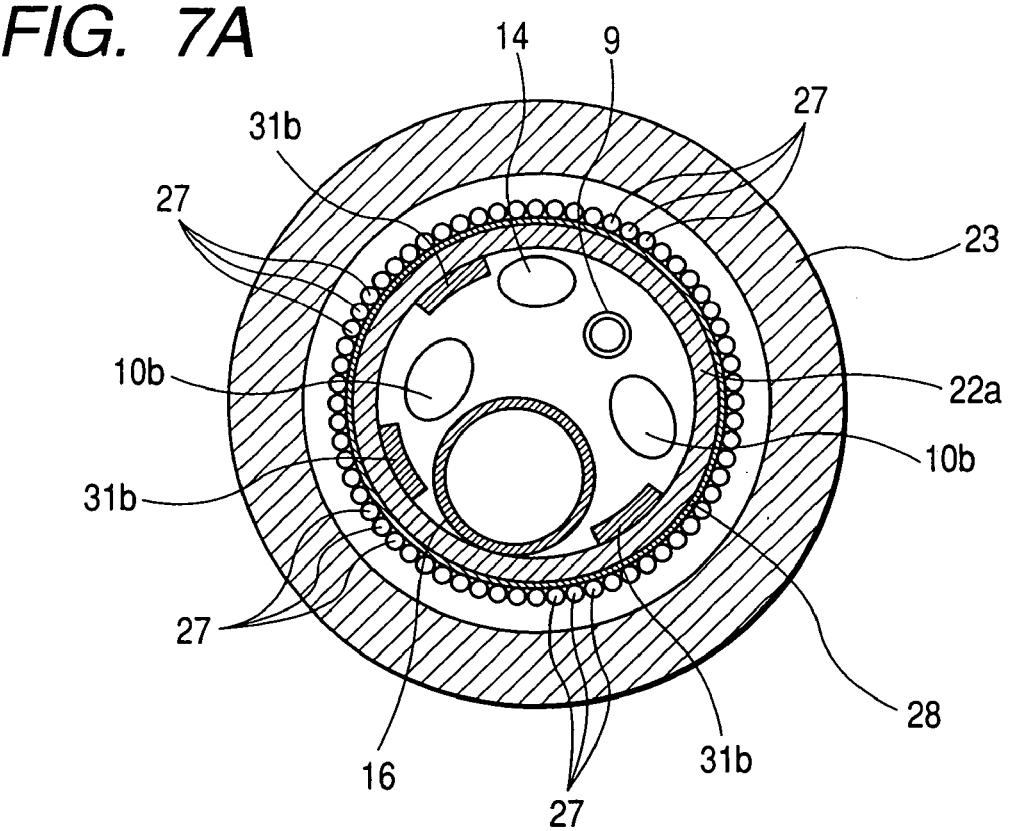
FIG. 7A is a cross-sectional view taken along line C-C of FIG. 4A.
Figure 7B:
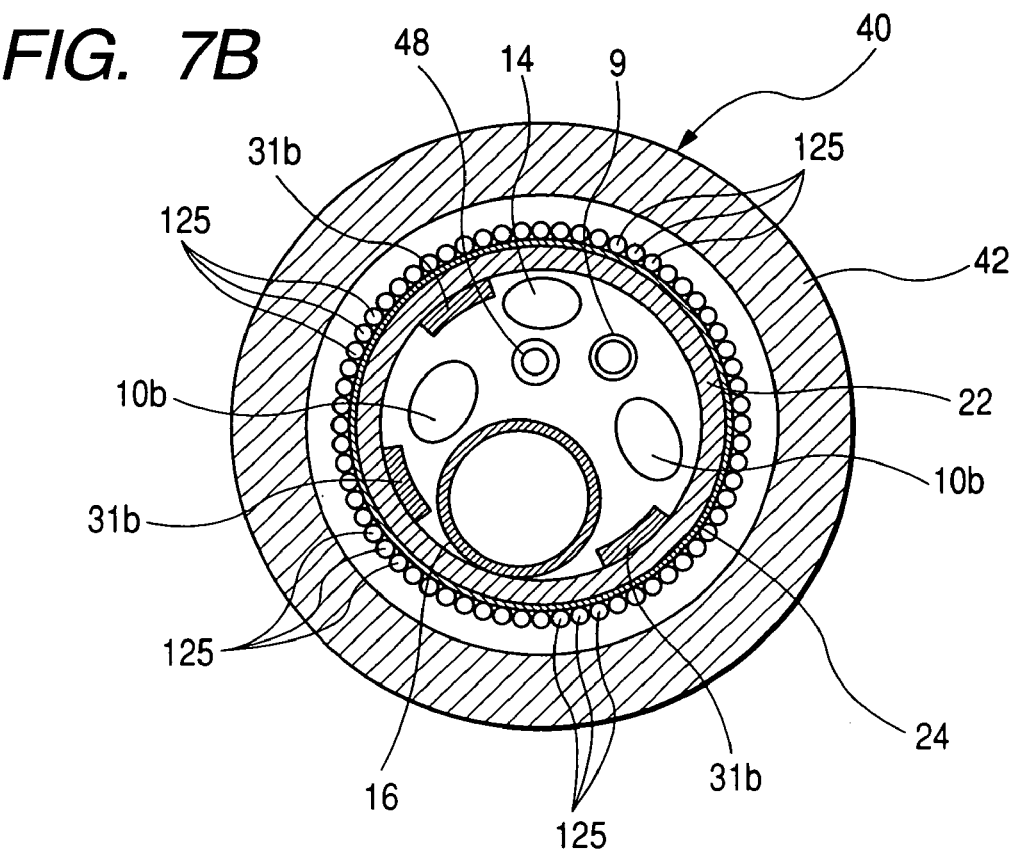
FIG. 7B is a cross-sectional view taken along line C'-C' of FIG. 4B.

In the first embodiment of the distal end of the insertion portion 2 (FIGS. 4A, 5A, 6A, 7A and 8A), each of the ultrasonic transducers 21 has two electrode 25 and 26, and the electrode 25 is a common electrode 25 common to all (or each predetermined number of) the ultrasonic transducers 21. The electrodes 26 are individually provided for the respective ultrasonic transducers 21. The common electrode 25 and the individual electrodes 26 of the ultrasonic transducers 21 are electrically connected to terminal sections of wiring patterns formed on a film substrate. As shown in FIG. 7A, a film substrate 28 is connected between the individual electrodes 26 of the respective ultrasonic transducers 21 and a predetermined number of cables 27 so that the cables 27 are respectively connected to the individual electrodes 26. In principle, the electrode 25 may be connected to one cable, and although not shown, the one cable is connected on the distal side of the ultrasonic transducers 21. A reduced-diameter section 22a is formed on the proximal side of the backing material 22, and the film substrate 28 is extended to the reduced-diameter section 22a so that the individual electrodes 26 of the ultrasonic transducers 21 are respectively connected to the cables 27 at the position of the reduced-diameter section 22a. The cables 27 for ultrasonic signals (including the cable for the common electrode 25) are extended to the connector 3c provided on the universal cord 3 and are connected to the ultrasonic observation device.

As described above, the ultrasonic wave transmission/reception unit 24 has an approximately cylindrical shape, and its inner circumferential surface forms a tunnel-shaped path. The members constituting the above-mentioned endoscopic observation unit are inserted through the tunnel-shaped path formed by the ultrasonic wave transmission/reception unit 24, and the proximal side of the ultrasonic wave transmission/reception unit 24 abuts on a joining member 30 which constitutes a joining section between the angle portion 2b and the distal hard portion 2c.

In the second embodiment of the distal end of the insertion portion 2 (FIGS. 4B, 5B, 6B, 7B and 8B), each of the ultrasonic transducers 21 has electrodes formed on its obverse and reverse sides, and a flexible circuit board 124 abuts on the reverse side, i.e., on a side where the ultrasonic transducers 21 are fitted to the backing layer 22, and a predetermined wiring pattern is formed on the flexible circuit board 124. A multiplicity of cables 125 are connected to the flexible circuit board 124, and each of the cables 125 is extended toward the proximal side of the insertion portion 2. Accordingly, the respective electrodes on the reverse sides of the ultrasonic transducers 21 are individual electrodes. In general, the number of the cables 125 is made equal to the number of the ultrasonic transducers 21 which constitute the ultrasonic transducer array 123, but the number of the cables 125 can also be reduced by short-circuiting lines from a plurality of ones of the ultrasonic transducers 21 on the flexible circuit board 124. In addition, the electrode on the obverse side of the ultrasonic transducers 21 is a common electrode common to all the ultrasonic transducers 21, so that although not shown, one cable is connected to the electrode. In addition, in the case where the individual electrodes are short-circuited, common electrodes are provided each of which is common to a predetermined number of ones of the ultrasonic transducers 21, and the common electrodes are provided as groups each corresponding to the predetermined number of ones of the ultrasonic transducers 21. Cables are respectively connected to these common electrode groups.

As described above, the ultrasonic transducer array 123 has an approximately cylindrical shape, and its inner circumferential surface forms a tunnel-shaped path. The members constituting the endoscopic observation unit are inserted through the tunnel-shaped path formed by the ultrasonic transducer array 123, and are fixed to the endoscope fitting member 18 positioned on the distal side from the ultrasonic transducer array 123 and covered with the distal cap 19. A distal section of the ultrasonic transducer array 123 abuts on the distal cap 19, while a proximal side of the ultrasonic transducer array 123 abuts on a joining member 30. The joining member 30 constitutes a joining section between the angle portion 2b and the distal hard portion 2c.

Furthermore, a bridge member 31 is provided in the inside of the joining member 30, so that a forward end ring 32a of angle rings 32 which constitute the structure of the angle portion 2b is joined to the connection member 30 and the bridge member 31. Accordingly, as is apparent from FIGS. 8A and 8B, the joining member 30 and the bridge member 31 are joined together by a plurality of screws 33, and the forward end ring 32a is joined to the joining member 30 and the bridge member 31 by a plurality of screws 34.

Figure 8A:
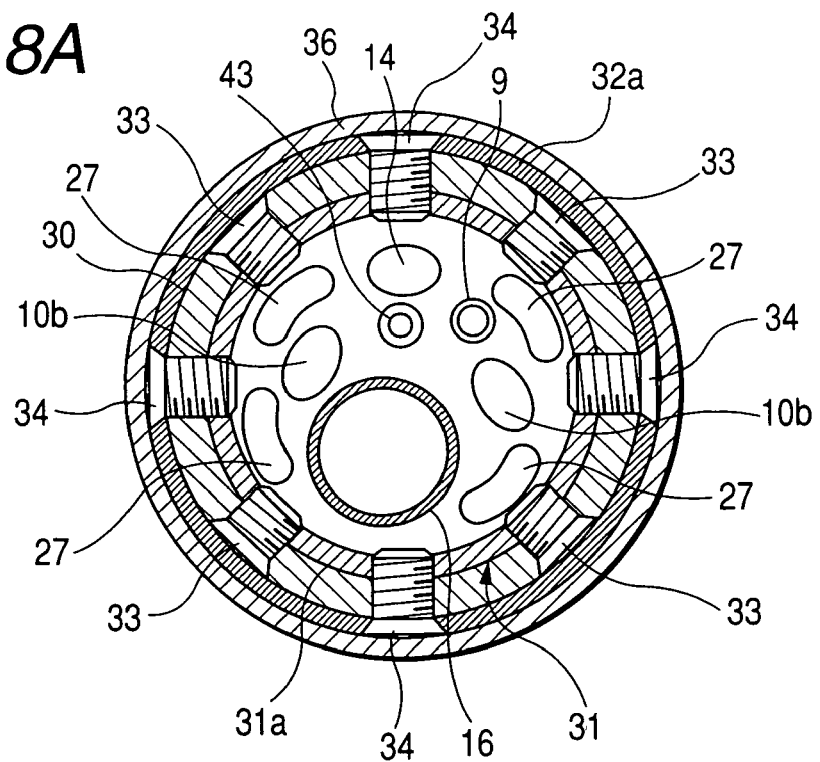
FIG. 8A is a cross-sectional view taken along line D-D of FIG. 4A.
Figure 8B:
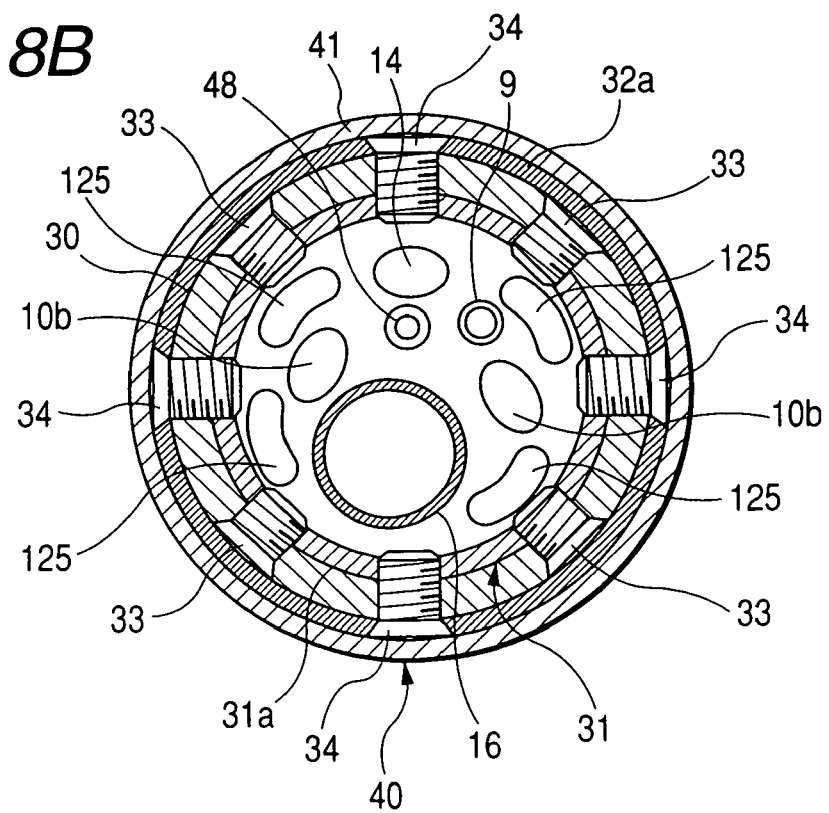
FIG. 8B is a cross-sectional view taken along line D'-D' of FIG. 4B.

Various members to be introduced into the insertion portion 2 are inserted through the joining section between the distal hard portion 2c and the angle portion 2b shown in FIGS. 8A and 8B. The two bundled light guides 10b, a video signal cable 14 (cable 125), and approximately four bundled cables 27 for ultrasonic signals are inserted through the joining section, and have arbitrary cross sections, respectively. In addition, the following members are inserted: a connection pipe 16 which constitutes a treatment equipment insertion path, a cleaning fluid supply tube 9, and a tube 43 for supplying an ultrasonic-wave transmission medium into a balloon 41 which will be described later.

Figure 9:
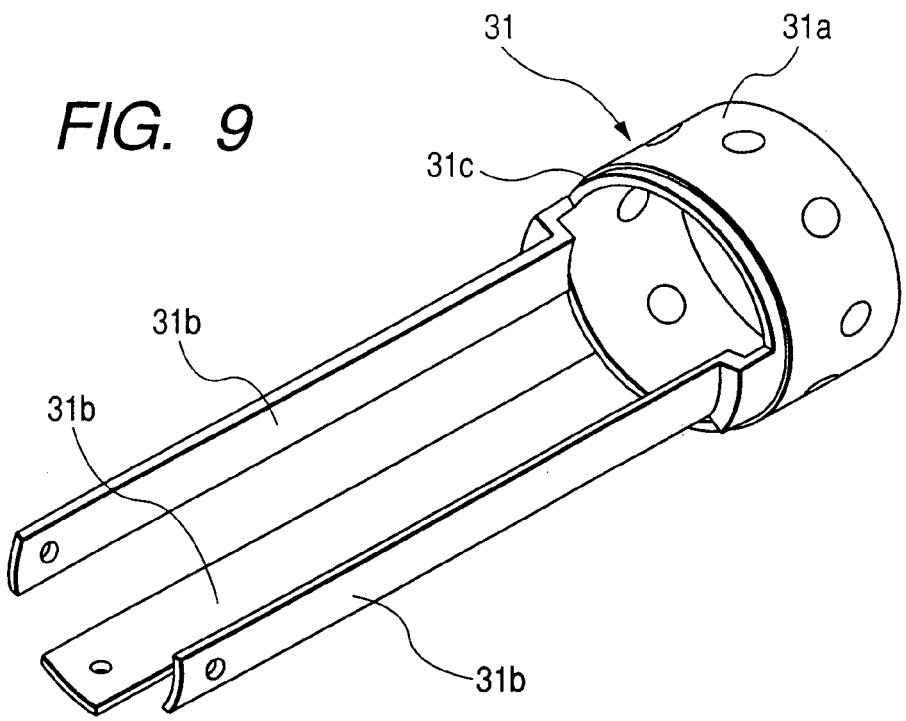
FIG. 9 is a perspective view of an external appearance of a bridge member of the ultrasonic endoscope according to the preferred embodiment of the invention.

The bridge member 31 serves the function of joining the joining member 30 arranged on the most proximal side of the distal hard portion 2c to the forward end ring 32a arranged in the angle portion 2b, the function of restricting the position of the ultrasonic wave transmission/reception unit 24 including the ultrasonic transducer array 123 in directions perpendicular to the axis of the distal hard portion 2c, and a joining function for a joining structure between the endoscope fitting member 18 and the distal cap 19. Accordingly, the bridge member 31 is formed of a metal such as stainless steel because the bridge member 31 is a member which needs to have a high strength and is not exposed to the outside. As shown in FIG. 9, a tubular section 31a of the bridge member 31 is joined to the joining member 30 and the forward end ring 32a of the angle rings 32 of the angle portion 2b by the screws 33 and 34, and a plurality of (in the present embodiment, three) joining arms 31b are extended from the tubular section 31a toward the distal end.

Accordingly, the ultrasonic wave transmission/reception unit 24 is positioned in directions perpendicular to the axis of the joining arms 31b by being fitted into the joining arms 31b, and the entire distal hard portion 2c is fixed in an assembled state by the distal ends of the respective arms 31b and the endoscope fitting member 18 being joined by screws 35. In addition, a step 31c is formed around the outer circumferential surface of the tubular section 31a of the bridge member 31, and the tubular section 31a extending from the step 31c toward the proximal side is larger in diameter than the step 31c. A step 30a is formed around the inner circumferential surface of the joining member 30, and the inner circumferential surface extending from the step 30a is larger in diameter than the step 30a. The ultrasonic wave transmission/reception unit 24 is clamped between the distal cap 19 and the joining member 30 by the steps 30a and 31c being joined together. When the opposite end surfaces of the ultrasonic wave transmission/reception unit 24 are respectively bonded to the proximal surface of the distal cap 19 and the distal surface of the joining member 30, the ultrasonic wave transmission/reception unit 24 is positioned in the direction of the axis thereof and is rotationally stopped, whereby the ultrasonic wave transmission/reception unit 24 is fixedly held at a predetermined position. A sheath layer 36 of the angle portion 2b is extended to a proximal outer circumferential section of the joining member 30, and the distal end of the sheath layer 36 is fixed to the joining member 30 of the distal hard portion 2c by a fixation mechanism 37 made of a bobbin and an adhesive.

The ultrasonic transducers 21 which constitute the ultrasonic wave transmission/reception unit 24 transmit ultrasonic waves into the body, and the ultrasonic wave transmission/reception unit 24 receives echoes from cross sections of tissues in the body. In order to restrain the attenuation of ultrasonic waves transmitted and received in this manner, annular concave grooves 40 are respectively formed at front and rear positions between which the ultrasonic wave transmission/reception unit 24 is provided, i.e., around the respective outer peripheries of the distal cap 19 and the joining member 30, and as is apparent from FIG. 2, a balloon 41 to be swollen by injecting the ultrasonic-wave transmission medium thereinto is fitted between the annular concave grooves 40. The balloon 41 is made of a tubular flexible film 41a, and fixation rings 41b to be fixedly fitted on the respective annular concave grooves 40 are provided on the opposite ends of the flexible film 41a. The fixation rings 41b are fixedly fitted so that tightening forces act on the respective annular concave grooves 40. A charge/discharge path 42 for charging or discharging the ultrasonic-wave transmission medium into or from the joining member 30 is formed in the joining member 30, and a tube 43 is connected to the charge/discharge path 42.

In this construction, an image of a body cavity of a subject is displayed on a monitor for displaying endoscopic images by inserting the insertion portion 2 into the body cavity, irradiating illumination light onto the body cavity from the illumination sections 10 which constitute the endoscopic observation unit, forming an image of the body cavity onto the solid-state image pickup device 13 by the objective lens 11a provided in the observation section 11, acquiring a video signal of the body cavity from the solid-state image pickup device 13 and transmitting the video signal to the video signal processing device, and performing predetermined signal processing in the video signal processing device. Accordingly, the operator can perform endoscopy on the state of the body cavity by watching the monitor.

If an area of interest such as a lesion is discovered as the result of the endoscopy, the ultrasonic wave transmission/reception unit 24 which constitutes the ultrasonic observation unit is moved to a position facing the area of interest. Namely, when the insertion portion 2 is advanced by a predetermined distance, the ultrasonic wave transmission/reception unit 24 is located at the position facing the area of interest. Then, the ultrasonic-wave transmission medium is supplied into the balloon 41 to cause the flexible film 41a to swell into close contact with an inner wall of the body cavity. In this state, the ultrasonic transducers 21 arranged in the circumferential direction to constitute the ultrasonic wave transmission/reception unit 24 are sequentially actuated to transmit ultrasonic pulses into the body and receive echoes. The ultrasonic transducers 21 can also be actuated sequentially one by one, but each plurality of the ultrasonic transducers 21 is actuated with a predetermined time lag so as to effect electronic focusing, for example. An electronic scanning method for the ultrasonic transducers 21 arranged in multiplicity is well known, and the description of such a method is omitted herein.

The echo signals acquired by the respective ultrasonic transducers 21 which constitute the ultrasonic wave transmission/reception unit 24 are transmitted to the ultrasonic observation device, and in the ultrasonic observation device, the echo signals are subjected to signal processing, so that tomographic information about the states of body tissues including the area of interest is acquired. This ultrasonic tomographic image is displayed on the monitor attached to the ultrasonic observation device. Accordingly, the operator can make a diagnosis as to whether a lesion is contained in the tissues, and the like.

Each member constituting the endoscopic observation unit is arranged on the inner circumferential side of the distal hard portion 2c, while each member constituting the ultrasonic observation unit is arranged on the outer circumferential side of the distal hard portion 2c. Each member constituting the endoscopic observation unit is inserted through the tunnel-shaped path formed by the ultrasonic wave transmission/reception unit 24, and is extended to the endoscope fitting member 18 and the distal cap 19 provided at the distal position of the ultrasonic wave transmission/reception unit 24. The distal cap 19 has an outside diameter approximately equal to that of the ultrasonic wave transmission/reception unit 24. Accordingly, a space which is not restricted by the dimensions of the tunnel-shaped path is ensured in front of the ultrasonic wave transmission/reception unit 24.

Figure 10:
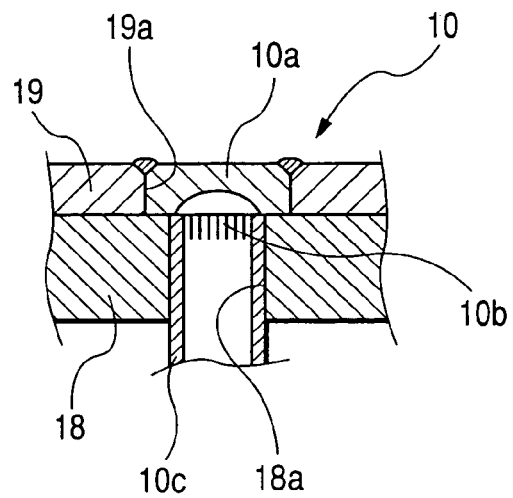
FIG. 10 is a cross-sectional view taken along line E-E of FIG. 10.

FIG. 10 shows a cross-sectional construction of a distal end of either one of the illumination sections 10. As described previously, each of the illumination sections 10 is made of the illumination lens 10a and the light guide 10b, and the light guide 10b is made of an optical fiber bundle and is bendable in itself and has a deformable cross-sectional shape. A predetermined length of the light guide 10b on the exit end side thereof is inserted into a connection metal 10c and fixed by an adhesive. The illumination lens 10a has a diameter larger than the outside diameter of the light guide 10b so that illumination light from the light guide 10b can efficiently exit through the illumination lens 10a without loss. The section of the light guide 10b that is inserted in the connection metal 10c is inserted in a through-hole 18a formed in the endoscope fitting member 18, and the illumination lens 10a is fitted in a through-hole 19a formed in the distal cap 19. The light guide 10b is deformable on the proximal side from the section of the light guide 10b that is inserted in the connection metal 10c.

Accordingly, a section which has the smallest diameter and is the most bendable and deformable from among the members constituting the illumination sections 10 is inserted through the narrowest path that is the tunnel-shaped path in the ultrasonic wave transmission/reception unit 24, so that the illumination sections 10 can be readily passed through the tunnel-shaped path. In addition, the illumination lenses 10a each having the largest diameter in a respective one of the illumination sections 10 are fitted to the distal cap 19 having a large outside diameter in front of the tunnel-shaped path, so that the illumination lenses 10a do not at all interfere with other members.

The solid-state image pickup device 13 and the circuit board 13a which constitute the observation section 11 are positioned in the inside of the tunnel-shaped path formed by the ultrasonic wave transmission/reception unit 24. The circuit board 13a is a plate-shaped member having a wide area, and is arranged so that its board surface is directed in the axial direction of the distal hard portion 2c and is arranged at a position near the center of the tunnel-shaped path. The objective lens 11a and the lens barrel 12 are arranged at a position near the peripheral section of the distal hard portion 2c. In addition, in the observation section 11 in which members having different shapes, such as the objective lens 11a and the lens barrel 12 as well as the solid-state image pickup device 13 and the circuit board 13a, are joined together, the inner circumferential distal end of the backing material 22 which forms the tunnel-shaped path in the ultrasonic wave transmission/reception unit 24 is arranged near the back surface of the prism 11b that is inclined obliquely forwardly from the solid-state image pickup device 13. Accordingly, the observation section 11 having a joined structure members having different shapes can be readily arranged without forming a special dead space in the tunnel-shaped path which is a narrow path, and the observation section 11 can be greatly protruded toward the outer circumferential side of the tunnel-shaped path at the distal position thereof, so that the observation section 11 can be arranged without interfering with the ultrasonic wave transmission/reception unit 24.

As described above, part of the members which constitute the illumination sections 10 and the observation section 11 are fitted in such a manner as to be partially protruded from the inside diameter of the tunnel-shaped path toward the outer circumferential side thereof, so that all the members can be reasonably fitted without increasing the diameter of the distal hard portion 2c, whereby the diameter of the insertion portion 2 can be made far thinner. In addition, the bridge member 31 is inserted into the tunnel-shaped path so that the ultrasonic wave transmission/reception unit 24 which is an approximately cylindrical member can be positioned in the directions perpendicular to the axis of the distal hard portion 2c in the inside of the tunnel-shaped path thereof, but in the inside of the ultrasonic wave transmission/reception unit 24, the bridge member 31 is made of the three joining arms 31b having narrow widths and is arranged so as to avoid an area in which the lens barrel 12 and the connection pipe 16 which constitutes the treatment equipment insertion path are inserted and an area in which the light guides 10b are inserted, so that the joining arms 31b do not at all become obstacles to the members constituting the endoscopic observation unit inserted through the tunnel-shaped path.

In other words, as shown in FIG. 3, assuming that R1 denotes the radius of the thickest-diameter section of the distal hard portion 2c, all the members constituting the endoscopic observation unit are positioned within a radius R2 in the largest radius R1, and the radius R2 which is an area in which the endoscopic observation unit is fitted corresponds to the position of a distal block in which the ultrasonic observation unit is not arranged. R3 denotes the inside radius of the tunnel-shaped path which houses the endoscopic observation unit in the ultrasonic observation unit, and the position of the radius R3 is closer to the proximal side than is the position where the radius of the endoscope fitted area reaches the largest radius R2, i.e., R3<R2. Accordingly, the radius R1 of the distal hard portion 2c can be made thin by the dimension of an area S in which the largest radius R2 and the radius R3 do not overlap each other.

As shown in FIG. 4B, in the second embodiment of the angle portion 2b, a predetermined number of angle rings 32 which are structure members for the angle portion 2b are pivotally joined together, and the forward end ring 32a is joined to the joining member 30 and the bridge member 31. The angle portion 2b is joined to the flexible portion 2a, and is covered with a net and a sheath layer. The sheath layer is constructed as part of an external sleeve 40 which covers the entire length from the angle portion 2b to the distal hard portion 2c. A proximal section of the external sleeve 40 is fixed to a transition section between the flexible portion 2a and the angle portion 2b by a bobbin and adhesion. A section which is provided to cover approximately the entire length of the angle portion 2b from the proximal section functions as a sheath layer section 41 in the angle portion 2b, while a section which covers a section in which the ultrasonic transducers 21 constituting the ultrasonic transducer array 23 is provided functions as an acoustic lens section 42 in the distal hard portion 2c. Namely, the external sleeve 40 is integrally provided with the sheath layer of the angle portion 2b and the acoustic lens which covers the ultrasonic transducer array 23.

The sheath layer is required to have stretchability, while the acoustic lens is required to be a medium which is lower in sonic speed than living bodies and is small in ultrasonic transmission loss. For example, silicone rubber is provided with all such characteristics and is the most advantageous as the external sleeve 40. It is also possible to use a material other than silicone rubber, for example, latex rubber or polyvinyl chloride.

In the external sleeve 40, the sheath layer section 41 has an approximately uniform thickness over its entire length, while the acoustic lens section 42 has an external surface with an arc convex shape which is the thickest in the central position of the ultrasonic transducer array 23 in the axial direction thereof. The inner circumferential side of the acoustic lens section 42 is formed in a cylindrical shape. The inner surface of the external sleeve 40 is coated with an adhesive. The inner surface is fixed to the net in the sheath layer section 41 and, in the acoustic lens section 42, to the ultrasonic transducers 21 which are arranged in a circumferential or arcuate shape.

As described previously, the proximal section of the external sleeve 40 is fixed to the vicinity of the boundary between the flexible portion 2a and the angle portion 2b, and the distal end of the external sleeve 40 is extended to the distal cap 19, and is fixed to the distal cap 19 by a bobbin and adhesion similarly to the proximal section of the external sleeve 40. Accordingly, in the insertion portion 2, the external sleeve 40 is provided so as to cover approximately the entire length from the angle portion 2b to the distal hard portion 2c.

Accordingly, as shown in FIG. 4B, a fixation section 43a is formed at the distal end of the acoustic lens section 42 of the external sleeve 40, and a bobbin and an adhesive section are formed in a transition section between the sheath layer section 41 and the acoustic lens section 42 of the external sleeve 40. A fixation section which is provided in the transition section functions as a tension transmission/interruption section 43b. Namely, when the angle portion 2b is operated to bend, the sheath layer section 41 is stretched by the influence of bending, but when the sheath layer section 41 is stretched, tension is interrupted so as not to act on a distal side from the tension transmission/interruption section 43b, so that a variation is prevented from occurring in the external shape of the acoustic lens section 42 and the characteristics of the acoustic lens are held in an unchanged state.

In addition, the ultrasonic transducers 21 which constitute the ultrasonic transducer array 23 transmit ultrasonic waves into the body, and the ultrasonic transducer array 23 receives echoes from cross sections of tissues in the body. In order to restrain the attenuation of ultrasonic waves transmitted and received in this manner, a balloon 44 to be swollen by injecting the ultrasonic-wave transmission medium thereinto is fitted to a section in which the ultrasonic transducer array 23 is fitted, as shown in FIG. 2B. The balloon 44 is made of a flexible film 44a, and fixation rings 44b are provided on the opposite ends of the flexible film 41a. In the distal hard portion 2c, the opposite fixation rings 44b of the balloon 44 are respectively brought in engagement with an annular concave groove 45 formed at a position near the distal end of the distal cap 19 and an annular concave groove 46 formed at a position between the tension transmission/interruption section 43b and the acoustic lens section 42 in the external sleeve 40. In the external sleeve 40, in order to form the annular concave groove 46, an annular concave groove 30b is formed around the outer circumferential surface of the joining member 30 which is provided to extend along the inner surface of the external sleeve 40.

Figure 11:
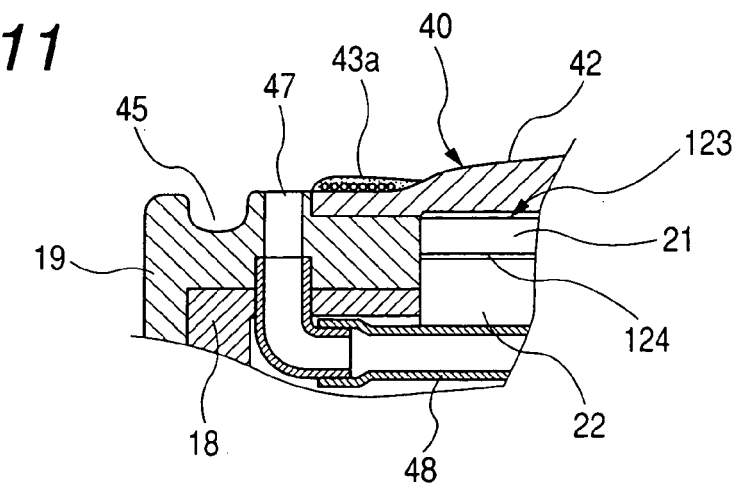
FIG. 11 is a cross-sectional view taken along line E-E of FIG. 2B.

Furthermore, as shown in FIG. 11, in the distal cap 19, a charge/discharge port 47 for charging or discharging the ultrasonic-wave transmission medium is formed between a section in which the annular concave groove 45 is formed and a section in which the distal end of the external sleeve 40 is fixed, and a charge/discharge tube 48 for charging or discharging the ultrasonic-wave transmission medium is connected to the charge/discharge port 47.

As described hereinabove, in the insertion portion 2, the sheath layer of the angle portion 2b and the acoustic lens fitted to the ultrasonic transducer array 23 are integrated, and the proximal section of the external sleeve 40 is fixed to the boundary between the angle portion 2b and the flexible portion 2a, while the distal section of the external sleeve 40 is fixed to the outer circumferential surface of the distal cap 19. In the insertion portion 2, the joining section between the angle portion 2b and the distal hard portion 2c is not exposed to the outside, and in addition, the ultrasonic transducer array 23 fitted to the distal hard portion 2c is not exposed to the outside, and the angle portion 2b and the distal hard portion 2c are completely covered with the external sleeve 40. Accordingly, a seal function for the above-described members can be fully achieved. In addition, the external sleeve 40 is fitted onto the section between the angle portion 2b of the insertion portion 2 and the distal hard portion 2c, and a process for a bobbin and adhesive coating needs only to be applied to three positions, i.e., the opposite ends of the external sleeve 40 and the tension transmission/interruption section 43b. Accordingly, ease of assembly is improved.

Figure 13:
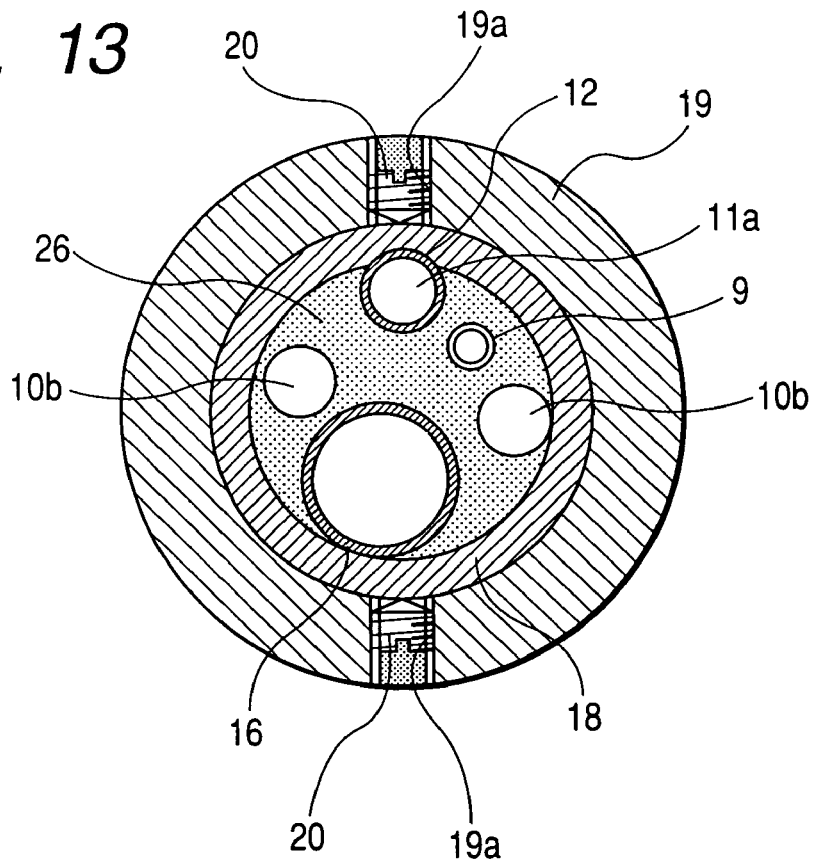
FIG. 13 is a cross-sectional view taken along line A"-A" of FIG. 12.
Figure 14:
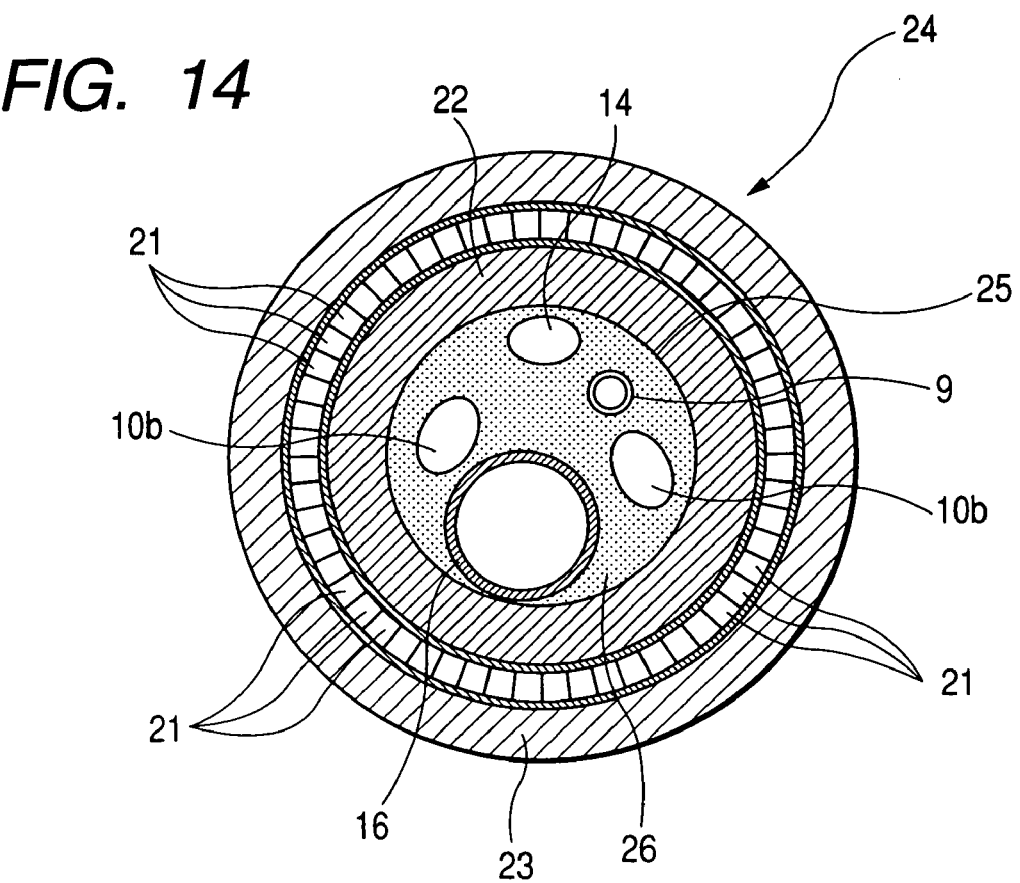
FIG. 14 is a cross-sectional view taken along line B"-B" of FIG. 12.

The third embodiment of the distal end of the insertion portion 2 will be described below with reference to FIGS. 12 to 14. In the third embodiment also, each of the members constituting the endoscopic mechanism is inserted into the tunnel-shaped path 25 which is formed by the inner circumferential surface of the backing layer 22 in the ultrasonic wave transmission/reception unit 24, and is extended from the ultrasonic wave transmission/reception unit 24 toward the distal end and is fixed to the endoscope fitting member 18 covered with the distal cap 19. A proximal end section of the endoscope fitting member 18 is formed as a large-diameter step 18a. A distal end section of the acoustic lens 23 which constitutes the ultrasonic wave transmission/reception unit 24 is extended to a position forward of the ultrasonic transducers 21 and is fitted on the large-diameter step 18a, and the ultrasonic wave transmission/reception unit 24 is fixed to the large-diameter step 18a by adhesion or the like. The proximal end of the ultrasonic wave transmission/reception unit 24 abut on a joining member 30 joined by screws 34 to a forward end ring 32a of an angle ring 32 which constitutes the structure of the angle portion 2b, and the proximal end and the joining member 30 are adhesively fixed to each other.

Figure 12:
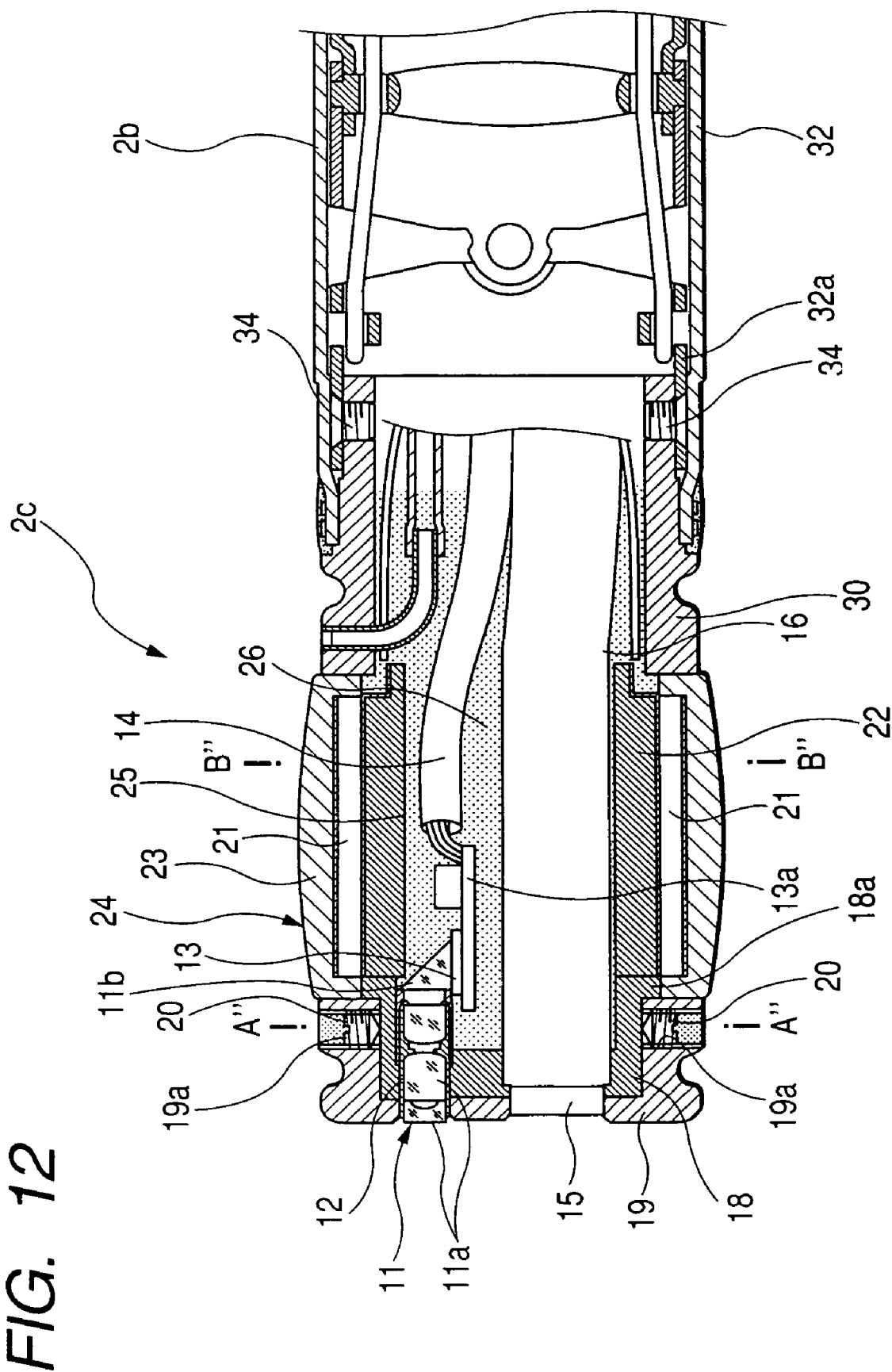
FIG. 12 is a vertical cross-sectional view of the distal hard portion (third embodiment)

Accordingly, as is apparent from FIG. 12, the narrowest section in the inside of the insertion portion 2 of the ultrasonic endoscope is a section in which the ultrasonic transducer array 24 is fitted, i.e., the section of the tunnel-shaped path 25 that is extended in the inside of the backing layer 22. As the endoscopic mechanism, the prism 11b which constitutes the observation section 11, the solid-state image pickup device 13 and the circuit board 13a thereof, and a distal end of the video signal cable 14 are positioned in the above-mentioned section. In addition, the light guides 10b (refer to FIGS. 13 and 14) which constitutes the illumination sections 10, the connection pipe 16 which constitutes a path through which a treatment equipment is to be inserted, and an air/water feed tube 9 are arranged in the inside of the backing layer 22. Accordingly, the size of the tunnel-shaped path 25 is restricted by the thickness of the backing layer 22. However, the size of the tunnel-shaped path 25 is set to a dimension enough to allow the above-mentioned endoscopic mechanism to be inserted through the tunnel-shaped path 25. If the outside diameter of the tunnel-shaped path 25 is set to a predetermined value, there is a case where the thickness of the backing layer 22 hinders the function thereof, i.e., the backing layer 22 cannot completely absorb echoes of ultrasonic waves transmitted from surfaces opposite to ultrasonic-wave transmission/reception surfaces.

Ultrasonic waves which travel from the ultrasonic transducers 21 toward the backing layer 22 are reflected at the interface between the backing layer 22 and an air layer. In addition, if a member different in acoustic impedance from the backing layer 22 abuts on the backing layer 22, echoes are also produced from the member.

For this reason, after each member constituting the endoscopic mechanism has been fitted in the inside of the tunnel-shaped path 25, a filler 26 made of the same material as the backing layer 22 is charged into the tunnel-shaped path 25 in a molten state. The filler 26 enters the space between each member constituting the endoscopic mechanism, in the inside of the backing layer 22. In addition, members which abut on or are close to the backing layer 22, such as the connection pipe 16 constituting a treatment equipment insertion path, can be displaced toward the center of the tunnel-shaped path 25.

The filler 26 made of the same material as the backing layer 22 is charged into the tunnel-shaped path 25 in the above-mentioned manner, so that the tunnel-shaped path 25 in which the backing layer 22 is formed is densely charged with the filler 26 so as to prevent substantial penetration of air.

According to the above-described construction, when ultrasonic pulses are transmitted from the ultrasonic transducers 21 which constitute the ultrasonic wave transmission/reception unit 24, ultrasonic waves traveling toward the backing layer 22 travel toward the inside of the filler 26 without being reflected at the inner surfaces of the backing layer 22. Accordingly, even if the thickness of the backing layer 22 is thin, reflections from the sides opposite to the transmission/reception surfaces of the respective ultrasonic transducers 21 do not occur.

The section in which the tunnel-shaped path 25 is provided is the distal hard portion 2c of the insertion portion 2. Accordingly, even if the filler 26 is charged into the section to fix the members inserted therein, special problems do not occur, and when impact or the like is applied to a distal end of the insertion portion 2, it is possible to protect the solid-state image pickup device 13 and the circuit board 13a thereof which constitute the observation section 11, as well as the video signal cable 14 extended from the circuit board 13a. Furthermore, it is possible to maintain the airtightness of the lens barrel 12.

The entire disclosure of each and every foreign patent application from which the benefit of foreign priority has been claimed in the present application is incorporated herein by reference, as if fully set forth.

What is claimed is:

1. An ultrasonic endoscope comprising:
an insertion portion comprising a distal hard portion which includes
an endoscopic observation unit arranged within the distal hard portion so as to include an observation field of view that extends distally from a distal end of the distal hard portion with a predetermined viewing angle in an axial direction of the distal hard portion;
an ultrasonic observation unit that includes a predetermined number of ultrasonic transducers arranged circumferentially on an outer circumferential section of the distal hard portion and having a circular or arcuate scanning range, wherein the ultrasonic observation unit comprises an ultrasonic-wave transmission/reception unit that includes a backing layer on an inner circumferential surface such that the backing layer defines an approximately cylindrical tunnel-shaped path; and
a distal block arranged on a distal side of the distal hard portion in the axial direction of the distal hard portion with respect to a location where the ultrasonic-wave transmission/reception unit is arranged on the distal hard portion, wherein the endoscopic observation unit is arranged in the distal hard portion such that the endoscopic observation unit passes through the tunnel-shaped path and a distal end portion of at least one optical member of the endoscopic observation unit is fixed to the distal block such that an outer circumferential portion of the distal end portion of the at least one optical member of the endoscopic observation unit protrudes, in the distal block, beyond an inside diameter of the tunnel-shaped path defined by the backing layer toward an outer circumferential side of the distal hard portion in a radial direction of the distal hard portion.

2. An ultrasonic endoscope according to claim 1, wherein the endoscopic observation unit include at least one of an illumination section and an observation section.

3. An ultrasonic endoscope according to claim 2, wherein the illumination section comprises an illumination lens and a light guide, wherein the illumination lens includes the outer circumferential portion that protrudes, in the distal block, beyond an inside diameter of the tunnel-shaped path defined by the backing layer toward an outer circumferential side of the distal hard portion in a radial direction of the distal hard portion, and wherein the light guide is arranged in the tunnel-shaped path such that a cross-sectional shape of the light guide is deformed such that the light guide includes at least two different cross-sectional shapes in the axial direction of the distal hard portion.

4. An ultrasonic endoscope according to claim 2, wherein the distal block comprises:
an endoscope fitting member comprising a metallic material; and
a distal cap fitted so as to prevent the endoscope fitting member from being exposed to the outside, so that the members of the endoscopic observation unit are fixed to the distal block, and
wherein at a position where the distal cap is fitted, at least one of the illumination section and the observation section is increased in diameter so as to partially protrude beyond the inside diameter of the tunnel-shaped path defined by the backing layer toward an outer circumferential side of the distal hard portion in a radial direction of the distal hard portion.

5. An ultrasonic endoscope according to claim 1,
wherein the insertion portion further comprises
an angle portion connected to the distal hard portion,
an acoustic lens fitted to surround an ultrasonic transducer array in which the ultrasonic transducers are arranged, and
wherein a sheath layer of the angle portion is fitted on the insertion portion as an integrated external sleeve.

6. An ultrasonic endoscope according to claim 5, wherein the external sleeve includes a tension transmission/reception section provided at a boundary between the sheath layer and the acoustic lens.

7. An ultrasonic endoscope according to claim 5, wherein the endoscopic observation unit comprises a plurality of members comprising at least an illumination section and an observation section, the endoscopic observation unit being disposed within the distal hard portion up to a distal end surface of the distal hard portion, wherein each of the plurality members of the endoscopic observation unit is fitted in an endoscope fitting section comprising a metallic material provided in the distal hard portion, and wherein a distal cover section which covers the endoscope fitting section is formed integrally with a distal end of the acoustic lens of the external sleeve.

8. An ultrasonic endoscope according to claim 1,
wherein the endoscopic observation unit comprises at least an illumination section and an observation section, the endoscopic observation unit being disposed within the distal hard portion up to a distal end surface of the distal hard portion;
wherein an endoscopic mechanism, which comprises the endoscopic observation unit and a plurality of other sections including a treatment equipment insertion channel, is inserted in an inside of the tunnel-shaped path; and
wherein a filler which is the same as or close to the backing layer in acoustic impedance is charged in a spatial area which is produced in a section of the distal hard portion where the endoscopic mechanism is arranged in the tunnel-shaped path.

9. An ultrasonic endoscope according to claim 8, wherein the filler comprises the same material as the backing layer and a solid-state image pickup device is provided in the observation section, at least part of the solid-state image pickup device being embedded in an inside of the filler.

* * * * *